(12) United States Patent
Zhang et al.

(10) Patent No.: US 10,927,396 B2
(45) Date of Patent: Feb. 23, 2021

(54) SPORE-BASED BIO-HYBRID MICROROBOTS AND THE AUTOMATED DETECTION SYSTEM FOR BACTERIAL TOXINS

(71) Applicant: The Chinese University of Hong Kong, Hong Kong (CN)

(72) Inventors: Li Zhang, Hong Kong (CN); Yabin Zhang, Hong Kong (CN); Lidong Yang, Hong Kong (CN); Kai Fung Chan, Hong Kong (CN); Lin Zhang, Hong Kong (CN); Ka Kei William Wu, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 22 days.

(21) Appl. No.: 16/175,024

(22) Filed: Oct. 30, 2018

(65) Prior Publication Data

US 2020/0131556 A1   Apr. 30, 2020

(51) Int. Cl.
| | | |
|---|---|---|
| *C12Q 1/04* | (2006.01) | |
| *G01N 1/10* | (2006.01) | |
| *A61B 5/145* | (2006.01) | |
| *C12Q 1/24* | (2006.01) | |
| *C12M 1/26* | (2006.01) | |
| *A61B 34/30* | (2016.01) | |

(52) U.S. Cl.
CPC ............ *C12Q 1/04* (2013.01); *A61B 5/14503* (2013.01); *C12M 1/268* (2013.01); *C12Q 1/24* (2013.01); *G01N 1/10* (2013.01); *A61B 34/30* (2016.02)

(58) Field of Classification Search
CPC .................................................. A61B 5/14503
See application file for complete search history.

(56) References Cited

U.S. PATENT DOCUMENTS

| | | |
|---|---|---|
| 8,765,399 B2 | 7/2014 | Riska |
| 8,768,501 B2 | 7/2014 | Fischer et al. |
| 9,868,991 B2 | 1/2018 | Wang et al. |
| 9,879,310 B2 | 1/2018 | Wang et al. |
| 2014/0087371 A1 | 3/2014 | Lu |

FOREIGN PATENT DOCUMENTS

WO   2014/044788 A1   3/2014

OTHER PUBLICATIONS

Cai et al., Austin J Anal Pharm Chem., 2014, 1(6):1-6.*
Dong et al., Analytical Chemistry, 2012, 84:6220-6224.*
Rieter et al., Angew. Chem. Int. Ed., 2007, 46:3680-3682.*

* cited by examiner

*Primary Examiner* — Bin Shen
(74) *Attorney, Agent, or Firm* — Kilpatrick Townsend & Stockton LLP

(57) ABSTRACT

Disclosed are materials, devices, methods and systems for the detection of target molecules in test samples using microrobots. The target molecules may be bacterial toxins. The microrobots may include biohybrid materials such as porous spore core, a middle layer coated on the spore core for the actuation and steering in a fluid and further conjugation with a functional probe, and a sensing probe anchored onto middle layer for attaching to the targeted molecules in a fluid to respond to fluorescent tracking. A system for detecting bacterial toxin, is disclosed and comprises an intelligent motion control system based on automated fluorescent recognition and detection methods, which can propel and guide the microrobots to realize the automated motion in a pre-designed path and perform the real-time monitoring when integrating with an inverted fluorescent microscope or a fluorescent emission multi-reader.

20 Claims, 15 Drawing Sheets

FIG. 4A
FIG. 4B
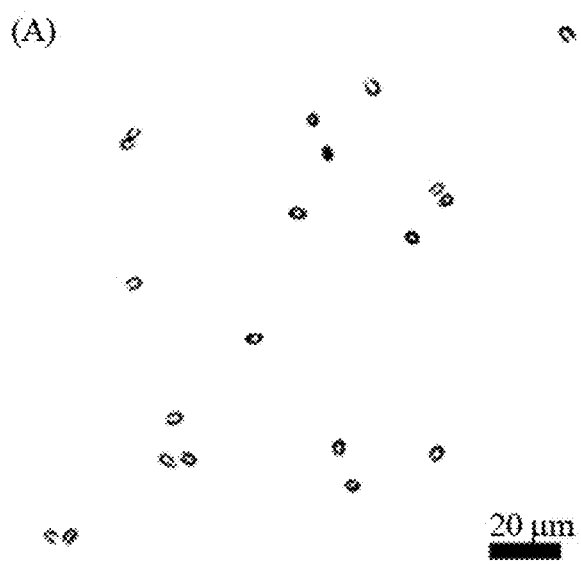
(A)
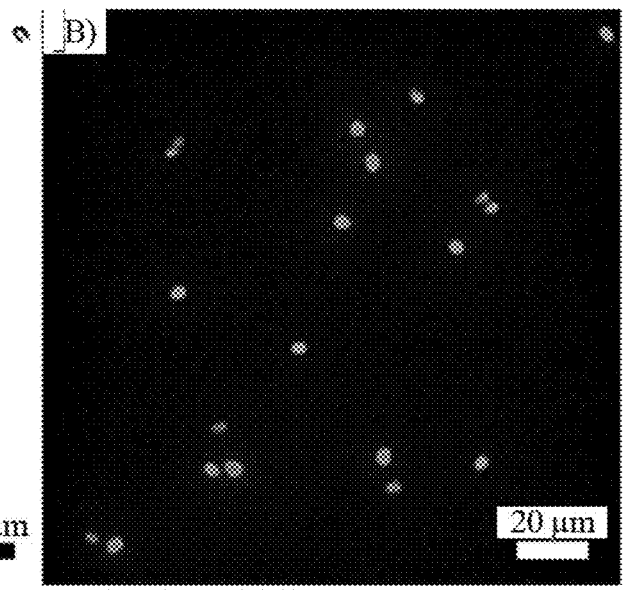
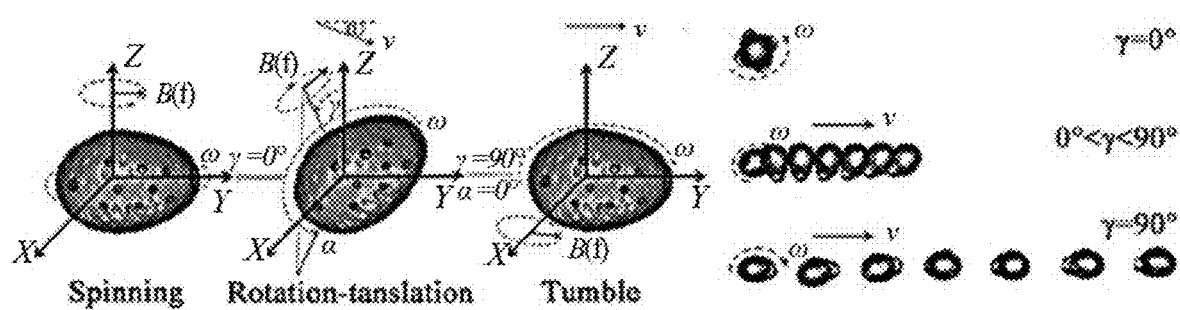
FIG. 5

SPORE-BASED BIO-HYBRID MICROROBOTS AND THE AUTOMATED DETECTION SYSTEM FOR BACTERIAL TOXINS

FIELD OF THE INVENTION

The present invention generally relates to the detection of microbial toxins and determination of the presence of bacteria using functionalized micro-robotic devices, automated fluorescent recognition and detection methods, and related detection systems.

BACKGROUND

There are millions of species of bacteria in the human body. Good bacteria can help the human body to break down big food molecules into useable fuel and produce vitamins to protect the body from diseases, while bad bacteria might make our body uncomfortable, and whose infection may trigger a series of bacteria-associated diseases and even death. To cure bacterial infections early, rapid, sensitive and early identification of specific bacteria in clinical specimens is advantageous. For example, *Clostridium difficile* (*C. diff*) is a gram-positive anaerobe and gastrointestinal pathogen responsible for hundreds of thousands of nosocomial infections in developed nations, whose infection can cause a series of *C. diff*-associated disease (CDAD), from mild diarrhea to even fatal pseudomembranous colitis. Commercially available diagnostic strategies of *C. diff* commonly include enzyme immunoassays (EIAs), cell culture cytotoxicity neutralization assay (CCNA), glutamate dehydrogenase (GDH) assay and molecular assays performed on stool samples, sigmoidoscopy or colonoscopy, and computerized tomography (CT) scan. These commercially diagnostic strategies either utilize a specific targeting detection of two toxins produced by *C. diff* through conjugation technique or perform the directing observation of suspected infected parts. However, these conventional screenings of *C. diff* are limited by high analytical cost, strong dependence on a reference, long process times (e.g. 24-48 hours), widely varying sensitivity and specificity, non-specific and low-accurate information from clinic images and the requirement of obvious infectious parts. Developing a simple, rapid, and real-time-monitoring diagnostic approach would be advantageous for clinical needs and helpful to the clinician for the prescription of an efficient treatment at the beginning of the infection.

SUMMARY

Embodiments of the present invention relates to materials, devices, methods and systems for implementing detection of target molecules, for example detection of toxins, in a fluid. The detection may be based on intensity-recognition and tracking of continuously moving fluorescent microrobots with a motion control system and image processor. The present invention includes methods of the detection of bacteria toxins performing at least one cycling step within tens of minutes, which may include an initial optimized selecting step and a continuous moving detection step. Furthermore, the present invention relates to all the materials, devices, and systems that are designed for the detection of bacteria toxin.

In one aspect, the present invention provides a device propelled in a fluid for detecting a target molecule, comprising a microrobot. Artificial micro-/nano-robots powered by various types of energy sources may be used for remote sensing strategies by utilizing the distinctive mechanical motion and easy functionalization inherited from micro-/nano-materials. Mobile sensing devices may offer real-time and on-site measurement, and also may cause an "on-the-move" reaction to accelerate the reaction rate produced by built-in sample solution mixing and improved contact from continuous movement. The introduction of motion dimension provides a solution to high-efficient chemo-/bio-sensing analysis. Embodiments of the present technology may include a biohybrid functionalized microrobot, to interact with target molecules, for example toxin molecules.

The biohybrid functionalized microrobot includes a core, a magnetic coating, and a detection probe coating. The core maybe a natural spore that has a unique and intricate three-dimensional sculptured architecture and can be cultivated in large quantities. On the surface of the core is a middle layer. The middle layer may be composed of hierarchical structure for actuating and steering in a fluid as well as anchoring a functionalized group. On the surface of the middle layer is a detection probe coating which may be composed of functionalized carbon quantum dots for attaching to target molecules, for example toxin molecules, in a fluid in order to produce a change in fluorescence for tracking. With the detection probe coating, the biohybrid functionalized microrobot is adapted to detect the presence of target molecules, in order to detect the presence of the biological targets in a specimen based on fluorescent changes with "on-the-move" reaction.

In embodiments, the biohybrid functionalized microrobots can be configured through a step-by-step coating technique. The as-obtained functionalized microrobots can be employed to detect a series of the target toxins based on fluorescent changes caused by continuous moving in a variety of media within tens of minutes. The microrobot can include a natural spore core, a middle layer coating, and a detection probe coating. The natural spore core can include the spore of any plants and fungi. The core may also be a synthetic core, and preferably a synthetic porous core. For example, the core may include mesoporous silica micro/nanostructures. The presence of the porous core is conducive to: the fabrication of functionalized microrobots on a large scale, the visual observation for tracking, and the high mass loading of detection probes for good sensitivity below the level of nanogram per milliliter comparable with the that of commercially available ELISA. The middle layer coating can include an actuated and steered structure and a functionalized component containing magnetic nanoparticles conjugated with a self-assembly monolayer molecule, which can provide the microrobot with magnetic properties for locomotion in a magnetic field generator and the functionality for further conjugation. The magnetic coating can include $Fe_3O_4$ nanoparticles, which can be extended to other magnetic particles such as nickel, iron and their oxides, and other magnetic metallic oxides. As used herein, the term "magnetic" refers to a material property of responding to a magnetic field, for example but not limited to paramagnetic and ferromagnetic. The detection probe coating can include the carbon dots with fluorescent emission and various specific groups or ligand molecules, for example, oligosaccharide targeting to repetitive oligopeptide, phenylboronic acid (PAPA) targeting to endotoxin, different aptamers binding to mycotoxins and ricin B toxin. The detection probe coating may also include other fluorescent probes with the same functionality of targeting detection. In embodiments, the detection probe coating may include different probe types having different specific targeting ability for detection of different targets. The detection probes in the detection probe coating can bind and form a complex with the target molecules, for example biological targets. Such a complex formation can be detected and the presence of the target molecules confirmed based on sensing fluorescent changing of the moving functionalized microrobot. The targets in a tested fluid can include bacteria toxins, for examples, toxin A and toxin B of *C. diff* toxin, endotoxins of Gram-negative bacteria, mycotoxin (ochratoxin A and fumonisine B1) from fungi in rotten foods, even and plant ricin B toxin.

In another aspect, the present invention provides a system of detecting bacteria toxin in a fluid based on functionalized microrobots together with automated fluorescent recognition and detection methods. The system can include mobile fluorescent microrobots as described above and a motion control system propelling the microrobot locomotion in a fluid in automated or manual operation modes. The system further includes an imaging device, for example an inverted fluorescent microscope or a fluorescent emission multi-reader, and can be directly applied to detect the presence of the toxin targets. The method includes the initial optimized recognition of the fluorescent microrobot and the following intensity estimation with the motion, realized by a motion control system.

In embodiments, the system can be configured using functionalized microrobots and a motion control system composed of a magnetic field generator, a controller box and a motorized sample platform for fluorescent observation. The motion control system can propel the functionalized microrobots swimming in various media for detecting the presence of a certain concentration of the target toxin based on the changing of fluorescent intensity induced by the reaction of "chemistry-on-the-move". The motion control system also can control the functionalized microrobots to locomote in manual or automated operation modes. A magnetic field generator provides an external rotating magnetic field, and include a plurality of electromagnetic coils and/or a rotating magnet. A controller box includes hardware and software to control the automated planning of motion path of the functionalized microrobot to complete the real-time monitoring of the fluorescent changes. A sample platform may include a motorized automated stage and a sample holder and may be used to move the sample for initial optimized recognition and fluorescent observation, as will be discussed in greater detail below. The system can be integrated onto inverted fluorescent microscope or with a fluorescent emission multi-reader for detecting the presence of the bacteria toxin in a biological or clinical specimen via sensing the complex formation based on accelerated fluorescent changes induced by the motion of the functionalized microrobots.

The subject matter described in this invention can be implemented in specific ways that provide one or more of the following merits. For examples, the disclosed functionalized microrobots can be produced on a large scale using low-cost natural spores via stepwise coating, which is superior to the conventional time-consuming and expensive template-assisted synthesis that commonly uses template like anodic alumina oxide templates to obtain desired structures through initial deposition and following the removal of the template. The disclosed functionalized microrobot include the intricate three-dimensional sculptured and porous structure of the spore providing active sites for attaching functional nanoparticles in a coating process and therefore providing contact reaction sites for a target molecule. Functionalized microrobots composed of magnetic nanoparticles can be actuated remotely under the simultaneous noncontact directional control by an external magnetic field, better than the fuel-propelled microrobots that require additional directional guidance. Functionalized microrobot also can be propelled in various fluids, including biofluids such as serum, mucus, urine, stool supernatant and gastric acid. Microrobots further show controllable swimming tracking trajectories. Functionalized microrobot comprising carbon dots may emit red light under the excitation with green light that can be tracked under a dark field. In embodiments, microrobots may include fluorescent nanoparticles other than carbon dots, for example polymer dots, silicon nanoparticle, molybdenum disulfide (MoS2) nanoparticles, Mxene nanoparticles, and combinations thereof. The fluorescent nanoparticles may emit the same or different wavelengths of light in response to the same or different wavelength of excitation as the carbon dots. The functionalization of the microrobots can be introduced by carbon dots with ligand molecules, e.g., oligosaccharides, aptamers, phenylboronic acid, and other toxin targeting molecules. Functionalized microrobots can establish effective motion-based detection of target molecules by observing the fluorescent changes with the motion. The movement of functionalized microrobots can enhance the solution intermixing and improve the diffusion rate of target molecules in a tested solution. Improved intermixing and diffusion lead to producing a faster, more favorable recognition reaction, compared with static microrobots only dependent on conventional diffusion. Functionalized microrobots can provide advantages of high detection efficiency, scaled-up synthesis, and trace sample analysis in the level of ng/mL in a variety of biomedically and clinically relevant applications. Functionalized microrobots with detection probes are less expensive and able to produce and possess distinctive motion performance compared to commercial probes (antibodies) of ELISA.

Motion control systems of the disclosed technology can make functionalized microrobots move in different modes. The motion control system may include an automate control operation mode wherein the motion of the microrobots is predetermined and is stored in a memory and executed to cause the stored motion to be executed. The motion control system may include a manual mode wherein a user vis a user interface may control the motion of the microrobots in real time. In embodiments, the automated control operation mode may have higher accuracy than the manual mode. For example, the automated control mode may include a control algorithm which causes the microrobots to follow a desired path with an accuracy error of less than 5 μm. Motion control systems of the disclosed technology can be used to search for microrobots having a the highest fluorescence of all the microrobots in a test sample by performing initial optimized recognition at the beginning of detection so as to enhance the detection sensitivity. The sensitivity is enhanced by excluding detection of microrobots with an initial low florescence, which in the detection step may be considered a quenched microrobot which may lead to false positive detection of a toxin.

Motion control system of the disclosed technology also can propel the microrobots continuously and automatically in the tested specimen within required times in pre-designed paths. In embodiments, the pre-designed paths cover an area within the field of view of the imaging device used to detect fluorescence in the detection process. The detection process is rapid and automated after the sample is placed in the sample holder. Further, the detection process is faster and simpler than standard enzyme-linked immunosorbent assay (ELISA). For example, the detection process may take in the tens of minutes, e.g. 10-30 minutes, whereas ELISA takes more than two hours. Unlike ELISA which is performed through a tedious incubation and rinsing process, the present technology only adds the microrobots into the tested supernatant and then evaluates the results using detection system.

The ability to selectively detect target molecules, for example bacteria toxins, using the motion control system equipped with functionalized microrobot can be utilized in many bioanalytical fields, e.g., including food safety, bio-/chemical-threat detection, and early diagnostic stage of bacteria-infected diseases. The details of one or more embodiments of the invention are set forth in the accompanying drawings and the description below. Other features, objects, and advantages of the invention will be apparent from the drawings and detailed description, and from the claims.

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive. Like reference symbols and designations in the various drawings indicate like elements.

FIGS. 4A and 4B show the optical image and fluorescent image of the disclosed functionalized microrobots under the green light excitation (excitation filter: 537-552 nm, emission filter: 582-637 nm).

FIG. 5 shows the schematic illustration of the disclosed functionalized microrobot moving in a rotating magnetic field and the corresponding motion modes at the different pitch angles.

DETAILED DESCRIPTION

Figure 1:
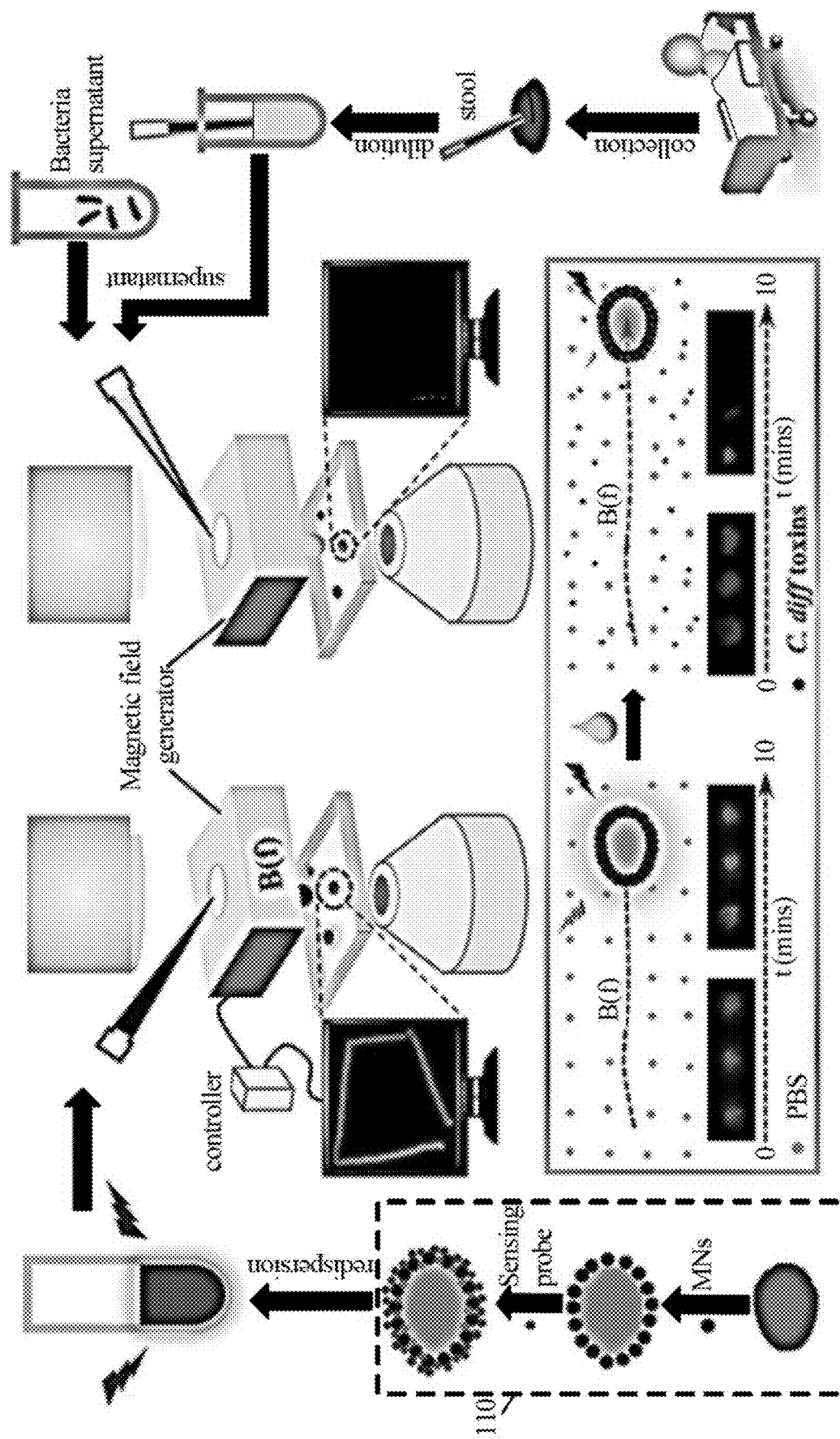
FIG. 1 is a schematic illustration of toxin detection using the disclosed functionalized microrobot in a motion control system equipped with an inverted fluorescent microscope.

The present invention may be understood more easily by reference to the detailed description, which forms a part of this disclosure. This invention is not limited to the specific materials, devices, methods or systems described and/or shown herein. Unless otherwise defined, all technical and scientific terms used herein have the same meaning as commonly understood by one of ordinary skill in the art to which this invention belongs. Although materials, devices, methods and systems similar or equivalent to those described herein can be used in the practice or testing of the present invention, suitable methods and materials are described below. The present invention involves two aspects, a functionalized microrobotic device and a resultant detection system based on automated fluorescent recognition and detection methods.

For example, the microrobots of the disclosed technology are capable of movement in a controlled manner and offer capabilities, e.g., including fluorescent tracking as a biomarker and motion detection of target molecule in a fluid. The disclosed micro-/nanomaterials and engineered microstructures may also be referred to as magnetic spores, fluorescent magnetic microrobots, steerable microrobots, and magnetic micromachines. In embodiments, the microrobots of the disclosed technology can be configured as sensing microrobots or micromachines that can detect the presence or absence of target molecules from biological or nonbiological specimens.

In embodiments of the present invention, biohybrid functionalized microrobots may be propelled in a rotating magnetic field in a tested fluid. The magnetically actuated motion makes the biohybrid functionalized microrobots have various applications including cargo delivery, biomedicine, environmental remediation, manipulation of small objects, and motion-based biosensing. For example, these functionalized microrobots provide the capability of detecting the presence of a target molecule in a specimen based on fluorescent changes with "on-the-move" reaction.

The ability to detect the presence of a targeted molecule can have implications, for example, in early screening, diagnosis and monitoring of bacteria, as well as in understanding the fundamental biology of bacteria-associated diseases. Functionalized microrobots can be implemented for in-vitro detection of bacteria toxins and even bacteria in a static or stationary fluid.

For example, the disclosed functionalized microrobot comprising a ligand molecule (e.g., an oligosaccharide) can enable the sensing of a targeted bacteria toxin having a receptor molecule (e.g., a repetitive oligopeptide), where a high affinity existing between the ligand molecule and receptor molecule triggers the fluorescent quenching. For example, oligosaccharide-functionalized microrobots can sense a target bacteria toxin based on the fluorescent change induced by a selective binding ability of attached oligosaccharide to the specific targeted oligopeptide of the *C. diff* toxin. A magnetic propulsion mechanism can enable continuous movement in a stable speed. For examples, the disclosed functionalized microrobot can be magnetically actuated continuously to detect the presence of a target *C. diff* toxin in a tested fluid, e.g., a static complex biological fluid. Such a continuous movement can enable effective detection of toxin, e.g., *C. diff* toxin in clinical stool supernatant due to enhancing the diffusion from "chemistry-on-the-move" reaction.

Exemplary implementations were performed to demonstrate the described functionalities and capabilities of the disclosed functionalized microrobot technology. For example, the detection of oligosaccharide-functionalized microrobot were shown to be highly specific to target *C. diff* toxins (toxin A and B) having the corresponding repetitive oligopeptides. Exemplary microrobot were functionalized with a specific ligand for the oligopeptide region expressed on a toxin secreted by bacteria. For example, an oligosaccharide-functionalized carbon dots can be attached to the modified surface of an exemplary microrobot to form an oligosaccharide-functionalized microrobot. Exemplary oligosaccharide-functionalized microrobots were utilized in exemplary implementations for detection of *C. diff* toxins expressing the combined repetitive oligopeptides (CROP). CROP is a protein being made up of multiple 19-24 amino acid short repeats and 31 amino acid long repeats, which is characteristic of toxins produced by *C. diff* (TcdA and TcdB). For example, CROP is generally regarded as a C-terminal receptor-binding domain of *C. diff* toxin to target the carbohydrate on the cells.

As shown in FIG. 1, a functionalized microrobot 110 can controllably move in a fluid by a magnetic field generator with a motion control system 120. Such a movement can be tracked under a dark field via its fluorescence. Based on the observation of the fluorescent quenching using an imaging device, such as an inverted fluorescent microscope or multi-reader, functionalized microrobots can detect the presence of a target toxin selectively and rapidly. For example, upon encountering target *C. diff* toxin in a fluid, e.g., bacterium culture medium, oligosaccharide-modified microrobot can be quenched by the *C. diff* toxin containing a repetitive oligopeptide. Fluorescent change caused by the binding of the repetitive oligopeptide to the oligosaccharide and corresponding functional groups can allow oligosaccharide-modified microrobot to perform a selective *C. diff* toxin detection in a pre-selected path. Functionalized microrobots can also exhibit unchanged fluorescence in the fluid without the addition of a target molecule.

Figure 2:
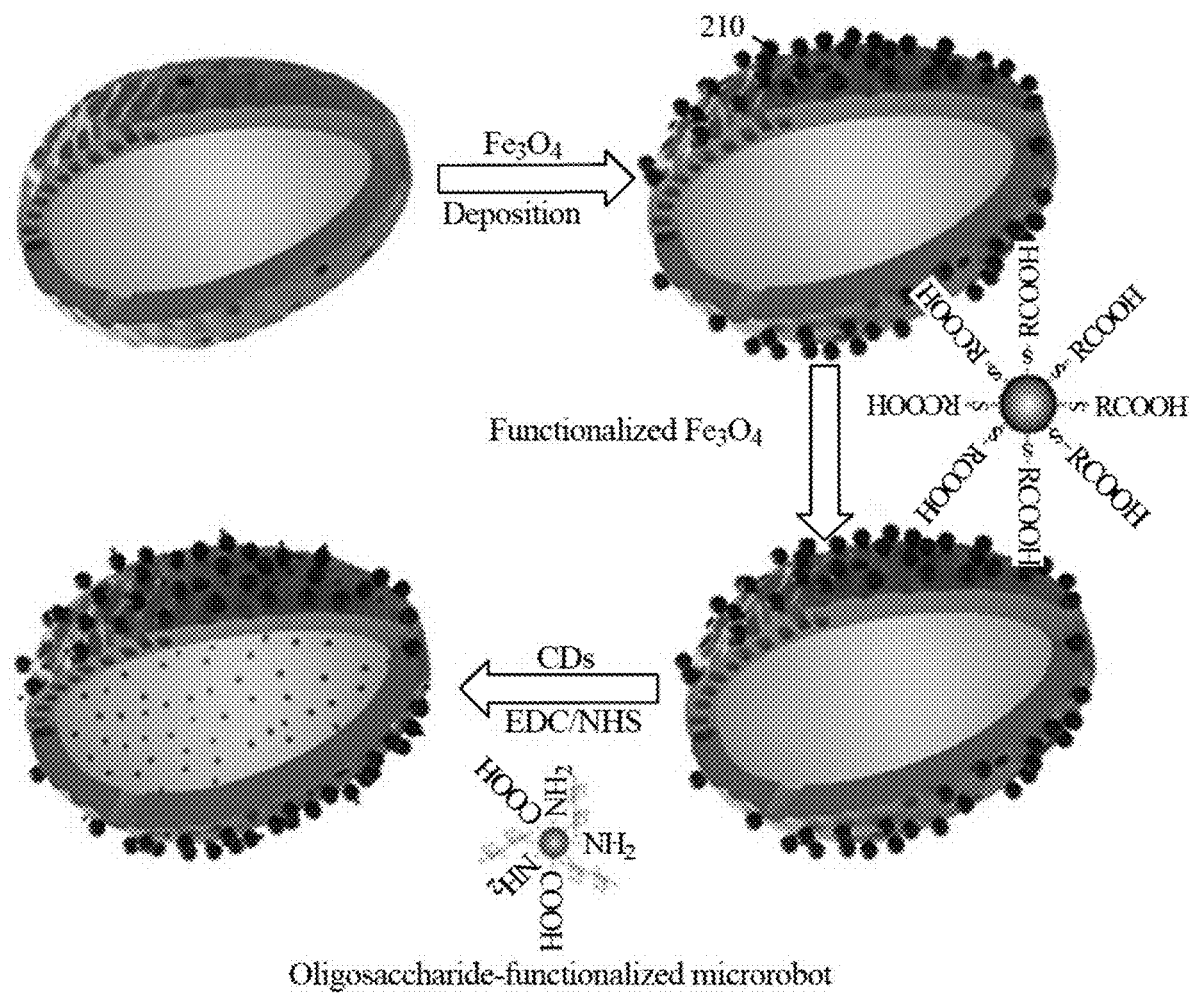
FIG. 2 shows a flow process of the preparation of the disclosed functionalized microrobot.
Figure 3:
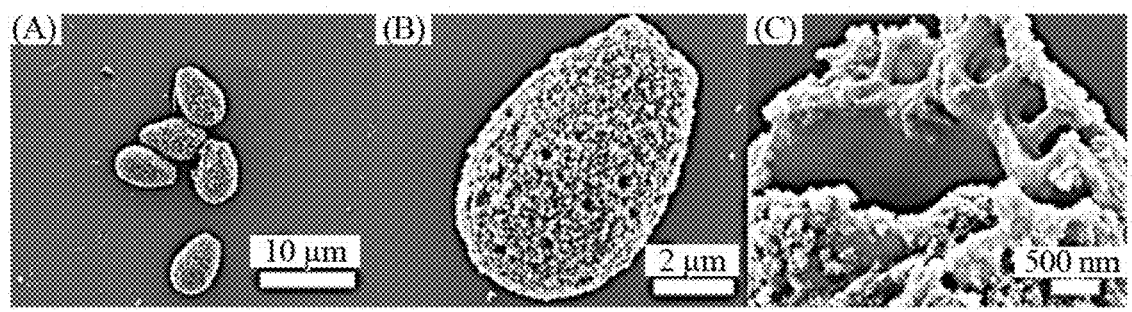
FIG. 3 shows the morphology and structure of the disclosed functionalized microrobots.
Figure 6:
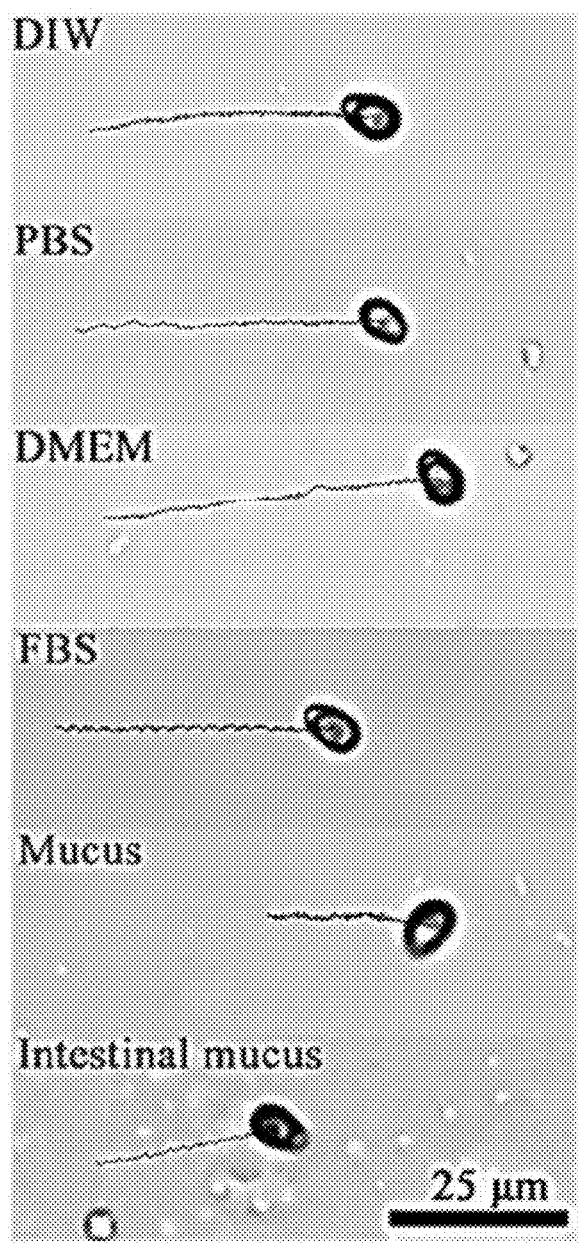
FIG. 6 shows motion trajectories of the disclosed functionalized microrobot in deionized water (DIW), phosphate buffer saline (PBS), cell culture medium (DMEM), fetal bovine serum (FBS), and mucus from pig stomach, intestinal mucus (Imucus) from pig guts over 5 s timeframes.

Fabrication of step-by-step deposition on cores, for example natural spores, can be implemented to produce the functionalized microrobot. Functionalized microrobots can be prepared by initially depositing magnetic coatings onto pretreated bio-templates, next being functionalized with self-assembled monolayers and finally encapsulating with functionalized fluorescent probes. As used herein the terms layer and coating refer to one or more volumes of a substance with a thickness and an area on a least a portion of a surface of a body or another layer or coating. The magnetic coating can enable actuation and navigation of the microrobots. Further functionalization with self-assembled monolayers can further attach detection probes or other structures. As shown in FIG. 2, a schematic illustration of an example step-by-step deposition technique is presented for fabricating microrobots of the disclosed technology. An example fabrication technique includes three steps, for example, depositing $Fe_3O_4$ nanoparticles onto *G. lucidum* spore templates, modifying the deposited $Fe_3O_4$ with thiolated self-assembled monolayers, and conjugating with oligosaccharide-functionalized fluorescent carbon dots. Schematic 210 shows an example of deposition of magnetic nanoparticles on natural spore cores. In embodiments, the cores may be synthetic. In embodiments the magnetic nanoparticles may have a maximum width between 20-80 nm. In some examples, magnetic $Fe_3O_4$ nanoparticles can be deposited onto the spore of a plant or fungi. In embodiments the deposited nanoparticles form a coating on the surface of the core. Schematic 220 shows the exemplary modification of magnetic nanoparticles for further conjugation, e.g., using 3-mercaptopropionic acid (MPA) to form the connection layer. Schematic 230 shows an exemplary of anchoring detection probe via EDC/NHS chemistry, e.g., conjugating with oligosaccharide-functionalized fluorescent carbon dots. The disclosed deposition technique can be implemented to produce magnetically-propelled functionalized microrobots. The structure, dimension and functionality of each component can be configured to engineer various performance parameters of the disclosed functionalized microrobots, including magnetic property, optical properties, targeting detection ability, and specific surface area. Examples of performance parameters include magnetic property (strength), optical properties (fluorescence or phosphorescence), targeting detection ability (specific fluorescence turn-on or turn-off), and specific surface area. In embodiments, the saturated magnetization of the microrobots is about 40 emu/g, which facilities propulsion in the magnetic field. In embodiments, the spore may range in size from 5 µm to 20 µm due to the variation of natural spores. In embodiments, the magnetic coating layer may have a thickness between 50 nm and 200 nm. In embodiments, the thickness of the magnetic coating layer may be dependent on the duration of the deposition time. In embodiments, the size of the magnetic nanoparticles may be between 20 nm and 80 nm across a long axis, for example as shown in FIG. 3. In embodiments, the size of sensing probes is about 1-10 nm. The sensing probes is very small relative to the core and magnetic coating, and therefore the thickness of the sensing probe coating may be considered negligible.

Figure 7A:
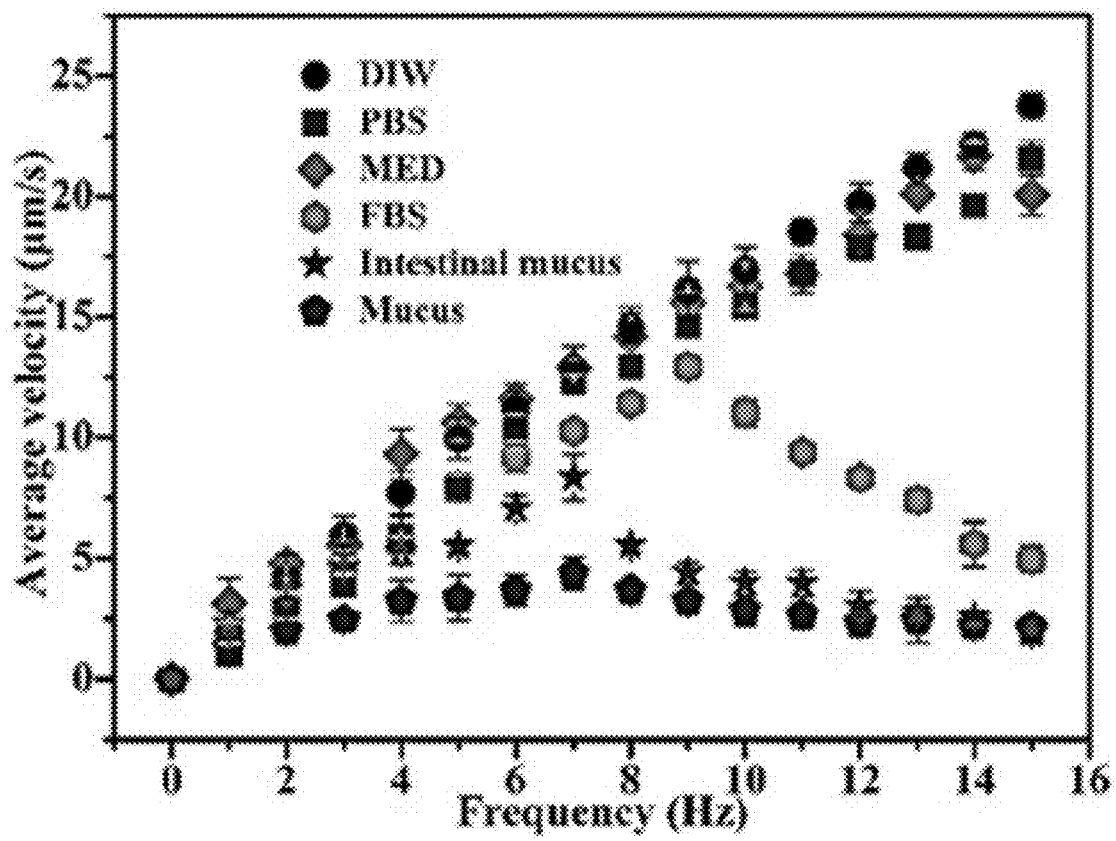
FIGS. 7A and 7B show the motion speed vs. frequency and speed vs. pitch angle curves of the disclosed functionalized microrobots.
Figure 7B:
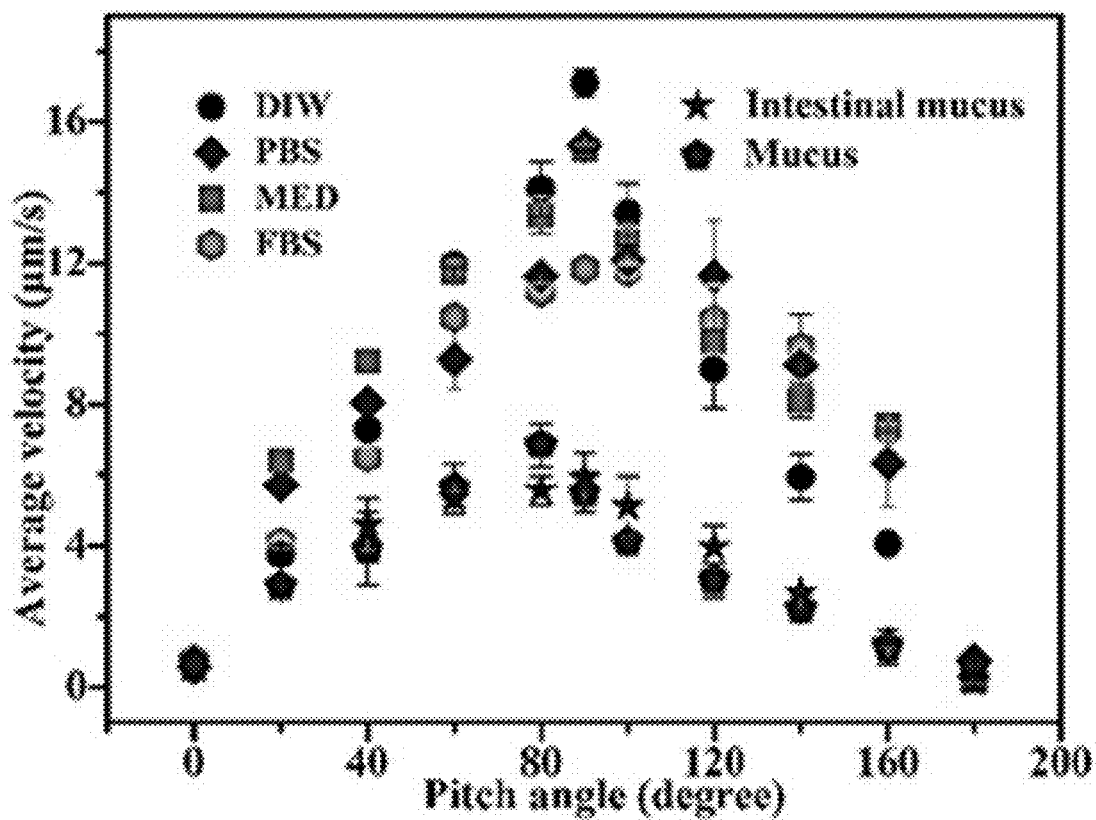
Figure 8:
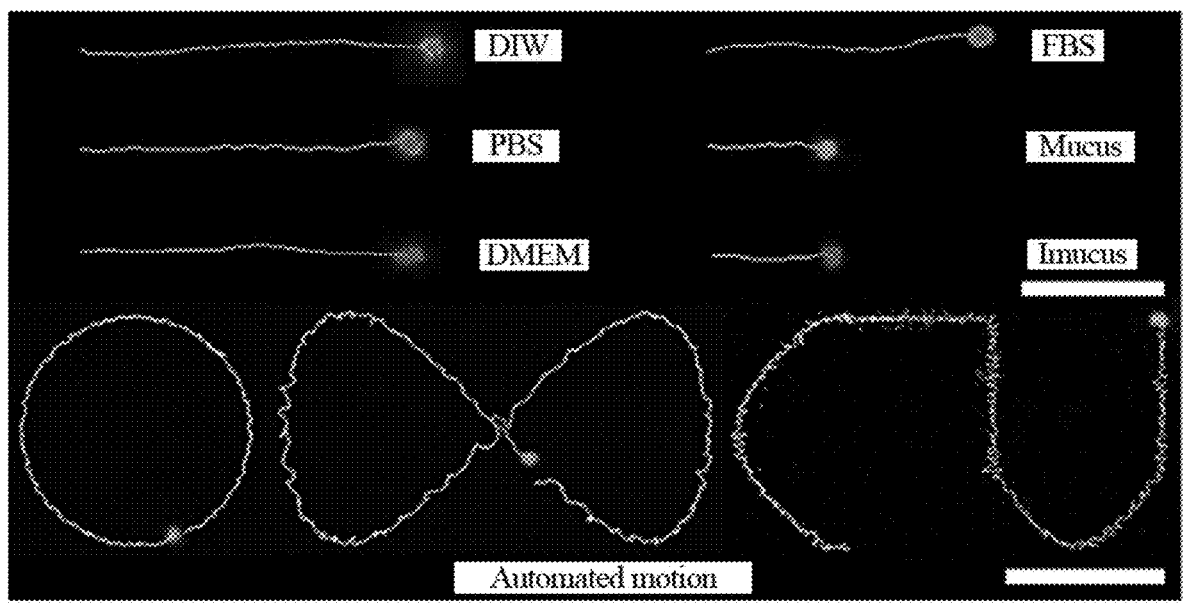
FIG. 8 shows fluorescent tracking trajectories of the moving disclosed functionalized microrobot in deionized water (DIW), phosphate buffer saline (PBS), cell culture medium (DMEM), fetal bovine serum (FBS), mucus from pig stomach, intestinal mucus (Imucus) from pig guts within 6 s in manual operation and the fluorescent tracking trajectories in DIW in the pre-set O-, ∞- and CU-like paths.

In embodiments, various types of natural spores can be used as spore cores. Furthermore, in embodiments synthetic cores may be used. The disclosed deposition or encapsulation techniques can be applied to obtain microrobots with various structures and dimensions. For example, a *Lycopodium* spore or a *G. lucidum* spore may be used. Other examples can include the incorporation (e.g., deposition) of an intermediate magnetic layer, e.g., nickel or iron or their oxide nanoparticles. Other exemplary design considerations can include a detection probe layer with different targeting functionality. For example, exemplary implementations that encapsulates microrobot with PAPA or related functional groups can achieve the targeting towards bacteria endotoxin. The exemplary design of the microrobot having a three-layer architecture can endow porous cores to multifunctionality, making the microrobots to detect the target molecules in a fluid.

An example of a fabrication process for a functionalized microrobot is described below. As noted herein, other steps and or materials may be used to fabricate a microrobot according to the present technology. The example fabrication process comprises taking the oligosaccharide-functionalized *G. lucidum* spore-based microrobot as an example. Firstly, *G. lucidum* spores are firstly pretreated to remove the impurities on the exine and internal core substances by sequentially ultrasonic treatment in 200 mL of absolute ethanol for 30 min, 200 mL of deionized water for 10 min, and washing with DIW several times for freezing dry. Then, spores are dispersed into 60 mL deionized water under the assist of ultrasonication and stirred, for example for 5 min, to form a brown suspension of spores dispersed in the deionized water. $FeSO_4$ is added to the above suspension and then stirred, for example for 20 mins. Through dropping 20 mL ammonia (25%-27 wt. %) within 10 mins, followed by sealing and further stirring for 2 h, the brownish black spore@$Fe_3O_4$ precipitation can be collected with a magnet. The collected precipitation can be washed with ethanol and deionized water several times and freeze-dried. After being freeze-dried to remove the water content, the brownish black samples can be dispersed into 200 mL of ethanol and stirred for 10 mins to form a homogenous suspension, followed by the addition of 0.2 mmol of 3-mercaptopropionic acid (MPA). The mixed suspension can be stirred for 10 mins and stayed at room temperature for 24 h. After being collected with a magnet, the carboxyl functionalized magnetic spores can be washed with ethanol, for example three times, to remove residual MPA, and then freeze-dried for the next preparation. After being freeze-dried to remove the ethanol content, 50 mg of functionalized magnetic spores can be dispersed into 60 mL of deionized water. Then, 0.5 mmol EDC and 0.5 mmol NHS can be added and stirred for 2 h to activate the carboxyl groups on the samples. After functionalized fluorescent carbon dots obtained by a facile hydrothermal treatment of 0.16 g of aspartic acid, 0.16 g of glucose and 0.16 g of p-phenylenediamine are added the mixed suspension and allowed to react at room temperature for 24 h under gentle stirring. The oligosaccharide-functionalized *G. lucidum* spore-based microrobot are obtained by using EDC/NHS coupling chemistry and collected by a magnet, washed with ethanol and deionized water several times and freezing-dried for further use. The example detailed fabrication described here also can be extended and applicable to the preparation of other functionalized microrobot, e.g., PAPA, aptamer, etc.

The prepared functionalized microrobot (e.g., oligosaccharide-functionalized microrobot or other attached ligands modified ones) is a device that is magnetically propelled in a fluid. For example, FIG. 3 shows an exemplary SEM images of functionalized microrobot composed of *G. lucidum* spore, $Fe_3O_4$ nanoparticles, and oligosaccharide-functionalized fluorescent carbon dots. As shown in FIG. 3A, droplet-like shaped microstructure has an average dimension of about 6-10 μm. As used herein, the term about refers to a 10% above and below the specified value or range of values. In embodiments, the core, either a naturally occurring core or a synthetic core, defines pores with diameters of about 100-400 nm. The pores are distributed on the surface of the core. FIG. 3B shows a layer of tens of nanometers nanoparticles, including iron oxides and carbon dots, coated on the surface of a microstructure. The broken structure in FIG. 3C shows a hollow cavity and a double-layer wall with a gap of 0.5-1 μm. Such an architecture consisting of retained pores together with the assembled nanoparticles, lead to high specific surface areas of about 12.96 $m^2/g$ with a wide pore size, thus providing more active sites for absorption and reaction.

The functionalized microstructure can be observed and tracked using for example a light field. The light field emits an excitation beam corresponding to the excitation wavelength of the functionalized microrobots. For example, green light excitation (excitation filter: 537-552 nm) may be used in a fluorescent inverted microscopy due to red fluorescent emission of the functionalized microrobots, as shown in FIG. 4. The functionalized microstructure also can be propelled in a magnetic field generator. For example, a rotating magnetic field of about 10 mT may be used to propel a microrobot with a magnetization strength above 10 emu/g in a common fluid, e.g. water or saline. In embodiments, higher strength of magnetic fields may be used, however due to Joule heat inside coils when used for a long time, higher strength magnetic fields may influence the motion of the test media. In embodiments, the controller of the rotating magnetic field may base the strength of the magnetic field on observed motion/velocity of the microrobots. For example, if microrobots are determined to be moving at a velocity lower than desired, for example due to a high viscosity of a fluids, the strength or frequency of the magnetic field may automatically be increased until the detected velocity of the microrobots reaches a desired velocity. In embodiments, the range of velocity may be from 2.0 μm/s to 40 μm/s, and may correspond to the viscosity of the fluid, for example the velocity may be at the low end of the velocity range for more viscous fluids, such as mucus, and may at the high end of the range for less viscous fluids, such as deionized water. In embodiments, the preferred velocity for detection of fluorescents is in a range from 5.5 μm/s to 16.9 μm/s.

In embodiments, the strength of magnetic field generator can be adjusted from 0 mT to 30 mT. The higher the strength of magnetic field is, the more efficient the propulsion is. However, high strength of the magnetic field is limited by the distance between the microrobots and coils and the current through coils which produce lager Joule heat. In embodiments, microrobots may be configured to be used in higher viscosity fluids or in weaker magnetic fields by increasing the magnetization strength of the microrobots. In embodiments, the rotating magnetic field operated at about 4 Hz.

In embodiments, microrobots may have locomotion caused by the magnetic field in three motion modes, spinning, rotation-translation, and tumble, as illustrated in FIG. 5. Furthermore, the effective magnetically propulsion can be maintained in various fluids, e.g., ranging from different biofluids to clinical supernatants. For example, the 5 second tracking trajectories of *G. lucidum* spore-based functionalized microrobot navigating in deionized water (DIW), phosphate buffer saline (PBS), cell culture medium (DMEM), fetal bovine serum (FBS), stomach mucus and intestinal mucus (Imucus) show excellent swimming performance. Moreover, the motion speeds in DIW, PBS, and cell medium DMEM increase with the frequency increasing, for example between 0 Hz to 15 Hz. The motion speeds in FBS, interstitial mucus and mucus firstly increase then decrease with the frequency increasing with a maximum motion speed between 7 and 9 Hz, as shown in FIG. 7A. The highest speed can be achieved in all media when moving in tumbling motion mode (90° pitch angle in FIG. 7B), possessing long moving displacement demonstrated by FIG. 5. The thickness of the magnetic layer can be increased by prolonging deposition time (e.g., 12 times than 2 h of initial deposition time) to facilitate more effective propulsion and navigation in biological media with high viscosity. The spore-based microrobot also show good fluorescent response for detection after the introduction of functionalized fluorescent carbon dots. For example, the fluorescence can rapidly decay with the spore-based microrobots moving within 10 min. Further for example, 6 second fluorescent tracking trajectories of oligosaccharide-functionalized *G. lucidum* spore-based microrobot navigating in DIW, PBS, DMEM, FBS, stomach mucus and Imucus are given in FIG. 8. Bright red emission of such microrobots does hardly fade down with the motion, prolonging time and the change of media, indicating good dynamic fluorescent stability. These results indicate that the oligosaccharide-functionalized *G. lucidum* spore-based microrobot shows good red fluorescent emission even if locomoting in different media. Moreover, the fluorescent features of functionalized microrobot together with the magnetic layer enable a magnetic remote control, guidance and tracking in the pre-designed route under a dark field. In embodiments, the path is an array of points distributed in the field of view of the microscope which has a dimension of 300 μm×300 μm. In embodiments, oligosaccharide-functionalized *G. lucidum* spore-based microrobots can achieve automatic fluorescent motion in pre-defined tracks. The pre-defined tracks may include geometric plane shapes such as an "O" (circle) or a "∞" (figure eight), and may include complex shapes with combinations of straight and/or curved trajectories, for example a CU trajectory as shown in FIG. 8. The pre-defined tracks may exhibit perfect paths with highly controlled precision. In the figures, the larger/brighter fluorescent dots in each path represent the present location of most of the microrobots. The lines represent the path that the microrobots sweep, or in other words the line shows the motion trajectory of the microrobots. In embodiments, the tracking error of the trajectory is smaller than half a body length of the microrobot, and therefore has a precision of about 5 μm.

Figure 9:
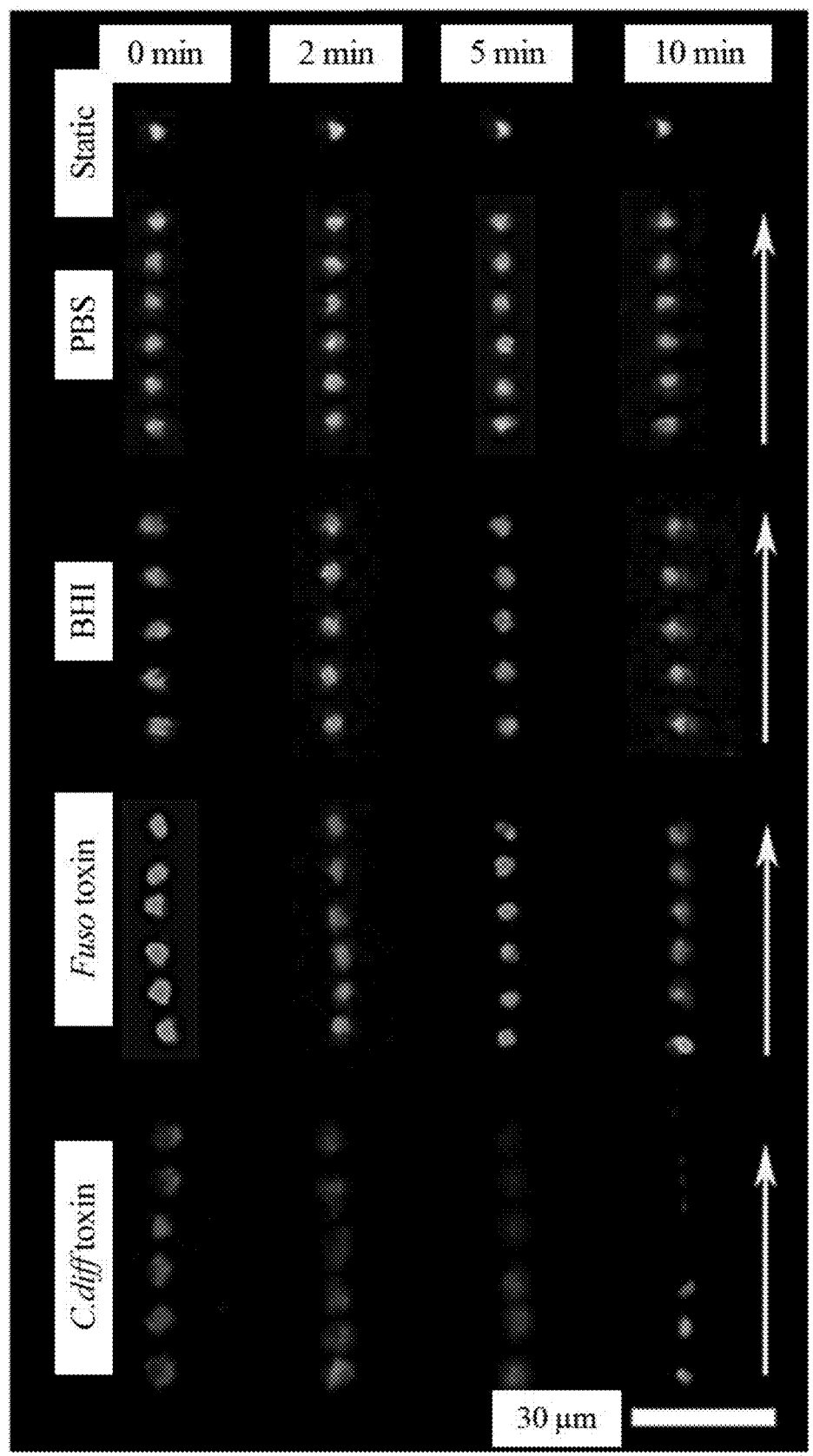
FIG. 9 shows fluorescent time-lapse images of moving and static functionalized microrobot in different supernatant from cultured C. diff bacteria.
Figure 10:
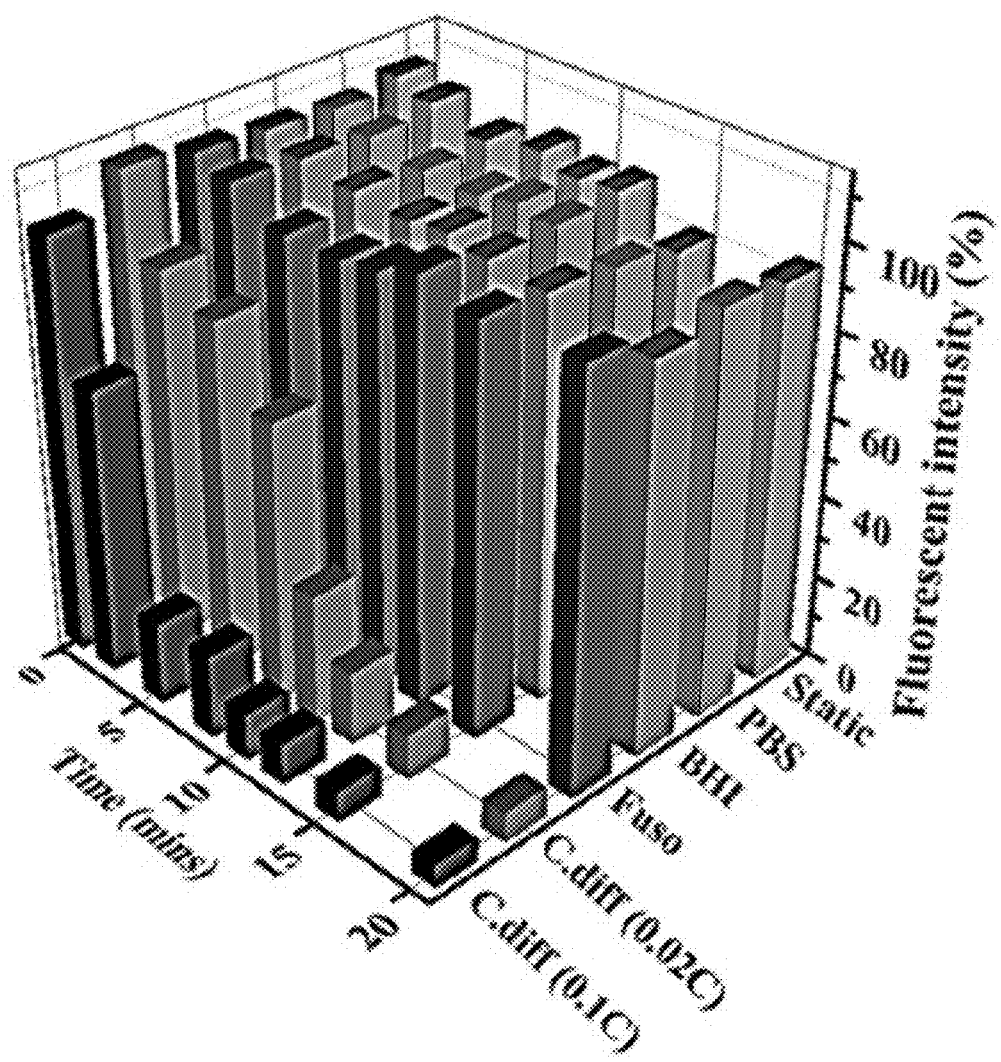
FIG. 10 shows the corresponding changing plot showing the fluorescence quenching of different samples (integrated density calculated by ImageJ program) at different times.
Figure 11A:
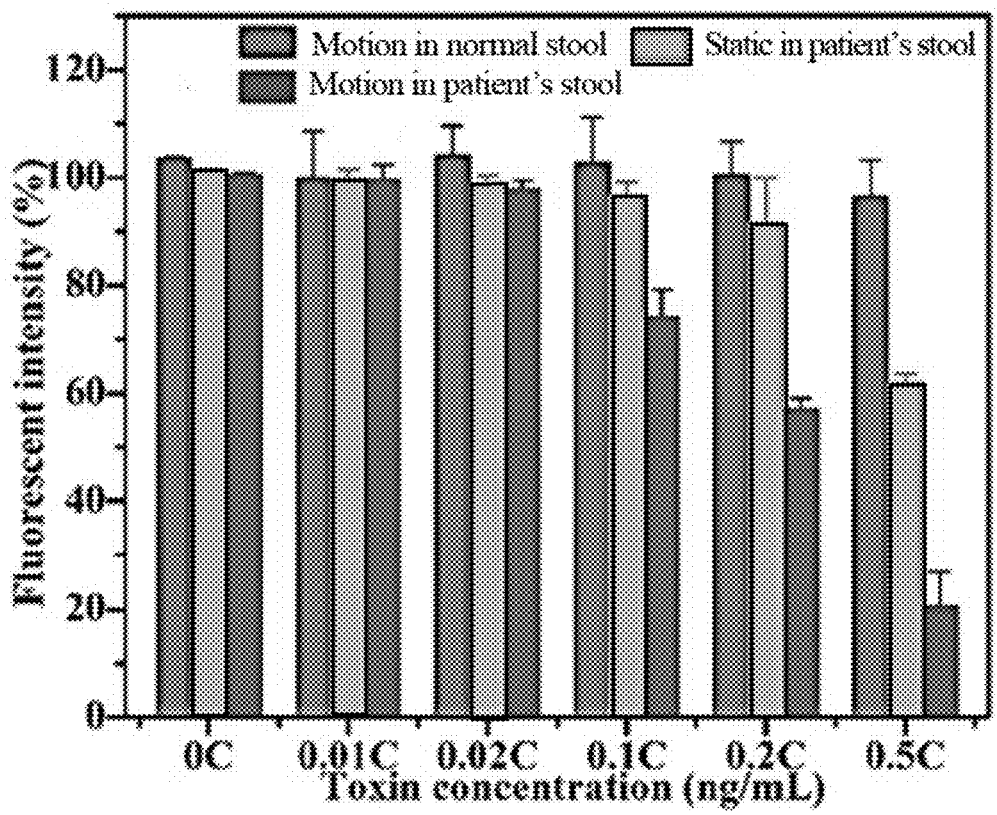
FIG. 11A shows the fluorescence quenching of mobile and static functionalized microrobots navigated for 10 min in different stool samples.
Figure 11B:
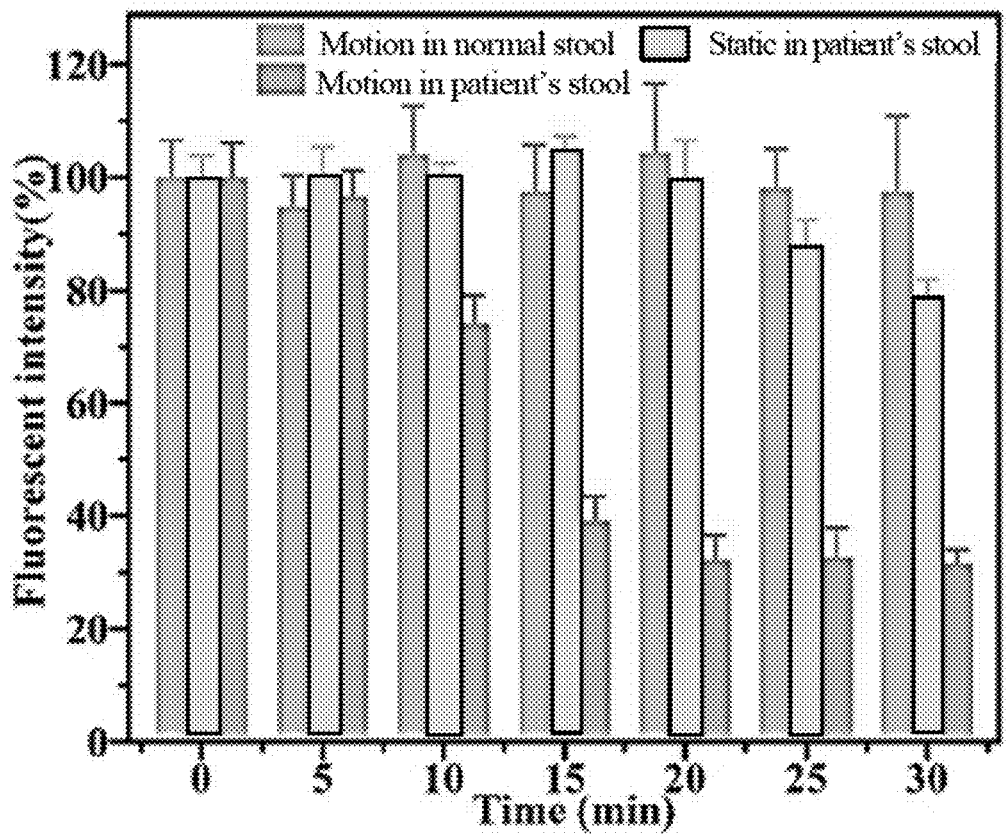
FIG. 11B shows the fluorescence quenching of mobile and static functionalized microrobots travelled for different times in 0.1 C stool samples.
Figure 12:
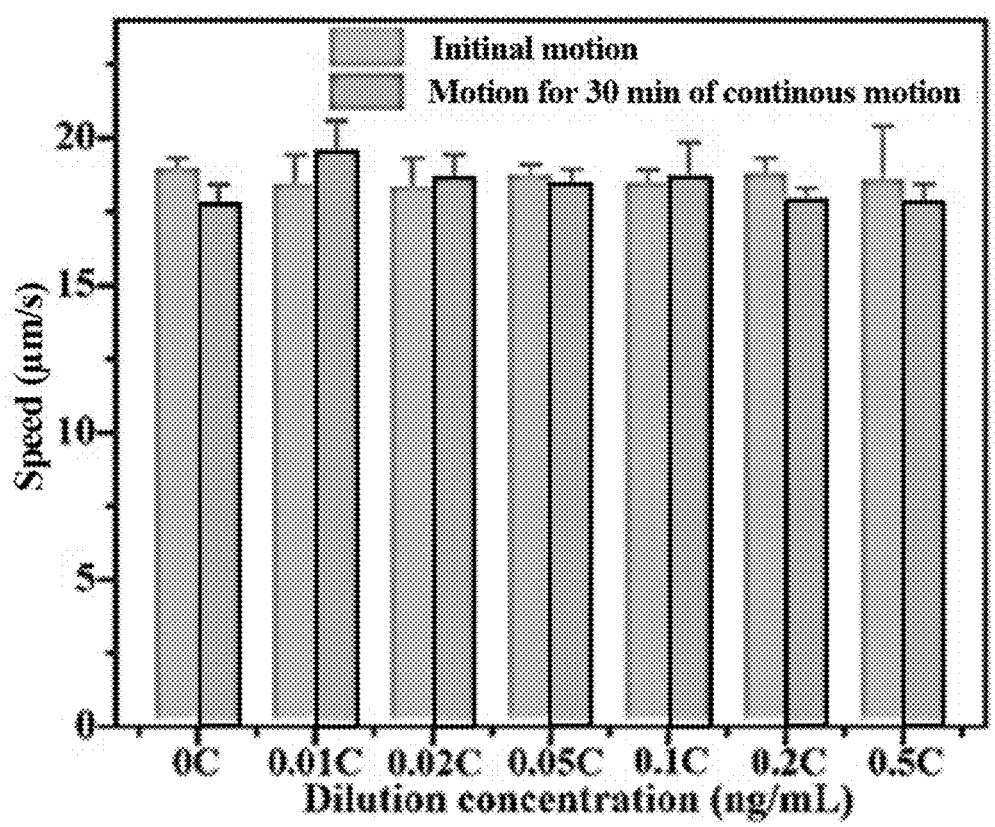
FIG. 12 shows 39 s tracking showing the propulsion of the disclosed functionalized microrobots in clinical stool supernatant at the beginning and after 30 min and speed changes of functionalized microrobots with moving time in clinical stool supernatant.

In view of excellent magnetically propelled ability and fluorescent response capability, the functionalized microrobots have been implemented for detection of the toxins, e.g., based on the selective and specific binding ability of functionalized microrobot. The microrobots can be encapsulated with carbon dots functionalized with targeting ligands (e.g., oligosaccharide or its specific groups) for highly specific toxin recognition. The microrobots can provide sufficient propulsive force for the efficient detection of target molecules in fluids, e.g., biological samples and complex clinical stool supernatant fluids. Microrobots can selectively detect bacteria toxins with simple pre-processing (including diluting and centrifugation) fluid samples and short detection time, e.g., simple dissolution of tested specimen and collection of supernatant as well as fast recognition within tens of minutes. The disclosed technology can also detect or sense other target molecules, for example toxins, chemical threats or biological molecules. For example, the oligosaccharide-functionalized *G. lucidum* spore-based microrobots can detect the toxins released from *C. diff* in biological samples. Time lapse images of such microrobots magnetically actuated in the supernatant containing bacteria toxins at a certain concentration are illustrated in FIG. 9. The oligosaccharide-functionalized *G. lucidum* spore-based microrobot navigated for 10 mins in the solutions contaminated by *C. diff* toxin shows instant fluorescence quenching while that magnetically navigated in the solutions contaminated by *Fuso* toxin displays no obvious fluorescent quenching. Microrobots magnetically propelled in PBS and BHI solution even for 10 mins display no fluorescent fading. The corresponding detection ability of the microrobots can be affected by various factors, e.g., motion mode, motion duration and concentration. For example, static functionalized microrobots do not show any fluorescence quenching with the time going in the solution with the same concentration of *C. diff* toxin compared with mobile microrobot. Even after staying in above control solutions for 20 mins, the fluorescence calculated from integrated density remains substantially stable. This not only illustrates the negligible interference effect of other solutes in tested samples, but also demonstrates that active motion shows high detecting efficiency than passive operation due to accelerated multiple "on-the-fly" reactions and enhanced fluid mixing. For examples, the fluorescence quenching appears quickly with the toxin concentration increasing, as shown in FIG. 10. The initial extent of fluorescence quenching of oligosaccharide-functionalized microrobots was directly related to the toxin concentration, decaying exponentially with the concentration increasing. Other exemplary implementations were performed that further demonstrate the detecting ability of functionalized microrobots to target bacteria toxins in practical application. For example, the exemplary implementations involved observing the fluorescent change of oligosaccharide-functionalized microrobots in clinical stool supernatant for the detection of *C. diff* toxins. FIGS. 11A and 11B show a changing plot of the fluorescence quenching of mobile and static oligosaccharide-functionalized microrobots navigated for different times and in various stool samples (integrated density calculated by ImageJ program). The fluorescent intensity of mobile oligosaccharide-functionalized microrobots (gray column) keep substantially stable in normal stool samples even if navigating for any times at various concentration of toxins. Static oligosaccharide-functionalized microrobots (cyan column) staying for 10 min or in 0.866 ng/mL of infectious stool samples display unobvious fluorescent quenching until at higher concentration (>0.2 C, C=8.66 ng/mL) or navigating for longer time (>20 min). The extent of fluorescence quenching is directly proportional to the toxin concentration in static or dynamic modes, which obeys Stern-Volmer equation. The exemplary mobile microrobot can detect the toxin in infectious stool samples effectively through sensitively fluorescent quenching. The disclosed microrobots also show stable continuous motion in clinic specimen, e.g., clinic stool supernatant. For example, the oligosaccharide-functionalized microrobots can continuously move even through long-term motion in real stool supernatant with various concentration and keep stable speed, as shown in FIG. 12. These suggest the anti-contaminated ability and efficient motion of the microrobots in clinical samples.

The disclosed microrobots include automated detection properties enabling continuous dynamic detection in fluids, including viscous fluids, e.g., bacteria culture media and clinical stool supernatant. The disclosed microrobots can have different targeting ability, e.g., by controlling ligand molecules, which can be implemented to detect other target molecules in the tested samples or to detect multiple target molecules. The disclosed microrobots can be employed in a rotating magnetic field, which can rapidly recognize the presence of toxin, e.g., *C. diff* toxins, within certain time interval in automated and continuous motion, in clinical pre-treated samples, e.g., stool.

In another aspect of the present technology, disclosed is a detecting system for a target molecule, for example bacteria toxin in a fluid, based on functionalized microrobots and automated fluorescent recognition and detection concepts. The disclosed system comprises a functionalized microrobot generating the sensing response to external stimulus with continuous movement and a motion control system applying the propulsion force and navigation to control the functionalized microrobot in manual and automated mode. The motion control system consists of a magnetic field generator, a controller box and a motorized sample platform. The magnetic field generator provides a rotating magnetic field to achieve the actuated motion of the microrobots within a test sample. The magnetic field generator can include an electromagnetic coil system and/or a rotating magnet. Further, in embodiments, other systems can be used to produce a rotating magnetic field, e.g., commercial Minimag and self-developed Magdisk. The control box includes a processor, storages, and a series of chipcards to deliver the executing command to the generator. The motorized sample platform is equipped for initial optimized recognition and the following detection in automated operation mode. The motion control system is coupled to an imaging device. The imaging device can include for example an inverted fluorescent microscope or a fluorescent multi-reader for the observation of fluorescent response and the evaluation of detection results. Through the feedback of observation results, the fully automated detection can be achieved by the as-formed whole loop system based on optimized recognition and automated detection algorithms. The system can be directly applied to detect the presence of the target molecules.

Examples of motion control system will be disclosed in the accompanying drawings and described in detail in the following.

Figure 13:
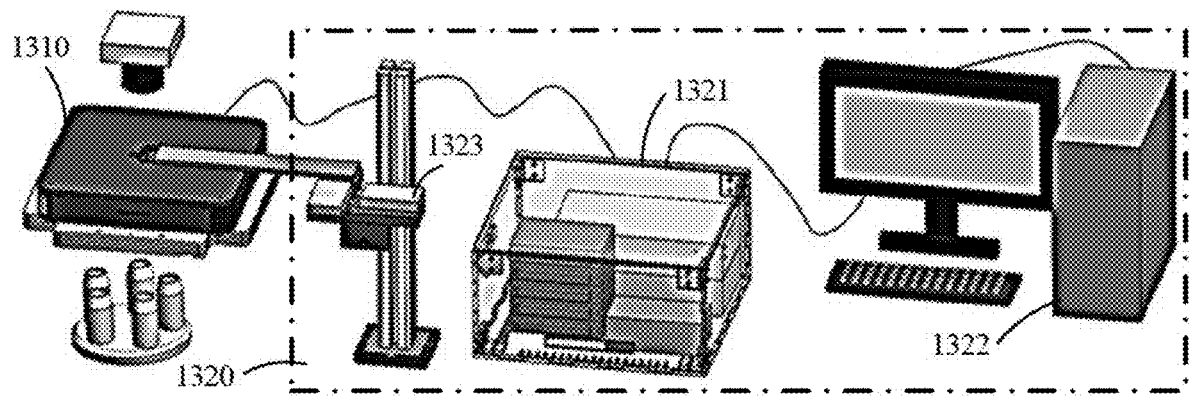
FIG. 13 shows a schematic illustration of a motion control system for detecting the bacteria toxin in different operation mode in real specimens.
Figure 14:
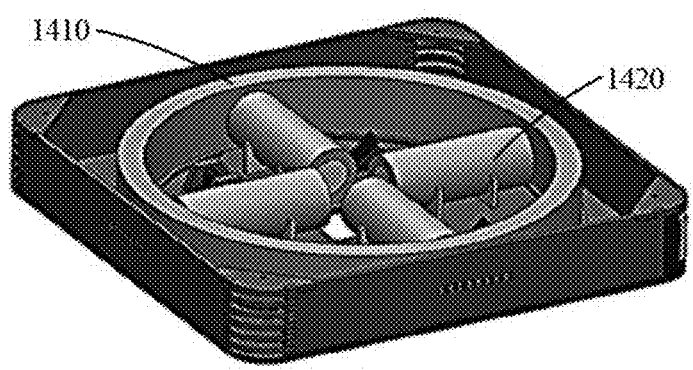
FIG. 14 is a schematic illustration of the example of magnetic field generator, e. g., self-developed 5-channels electromagnetic coil system, for propelling the disclosed functionalized microrobots.

FIG. 13 is a schematic diagram illustrating a motion control system for detecting the presence of the target molecules. The motion control system is composed of a magnetic field generator 1310 for magnetically-propelled functionalized microrobots and a controller box 1320 for steering their motion. In embodiments, the controller box, also referred to as the controller, contains amplifiers and a power supply which provide dynamic currents to the coils so that the magnetic fields that steer the microrobots are generated. The controller box sends signals to the magnetic field generator and the motion controller to simultaneously steer the microrobots. The magnetic field generator may generate a rotating magnetic field. Various electromagnetic coil system can be directly used as a magnetic field generator. For examples, a minibox-like, 5-channel apparatus including an outer coil 1410 and four identical planar coils 1420, as shown in FIG. 14, also called Magdisk below. Two pairs of planar coils are arranged orthogonally to form the magnetic field with the magnetic field vector of x-axis and y-axis. The outer coil surrounding them is responsible for the magnetic vector of z-axis. Soft magnetic iron cores used in the planar coils is to increase the maximum field strength achievable. The resulting Magdisk can generate the rotating, oscillating and gradient magnetic fields, which can realize motion control of magnetic microrobots with 5DOF (3 R+2 T) with its positioning precision reaching sub-cellular level.

The controller box 1320 includes a hardware system and a software system. The hardware includes a series of controller hardware 1321 executing the instruction set from software and a computer 1322 equipped with a sensor card for installing the software. Users can modify the parameters (direction angle, pitch angle, frequency and field strength) of the desired magnetic field via a user interface, e.g. a display, a keyboard and a mouse. In embodiments, the direction angle, pitch angle, frequency and field strength are modifiable to control the motion direction and speed of microrobots. For example, the hardware system of Magdisk consists of five servo amplifiers, two power supplies (36V, 9.7 A) and a digital-analog converter (DAC). The amplifiers are used to convert the voltage signal generated from the sensor card to current signal for the magnetic field generator. For examples, the servo amplifiers used in Magdisk are Maxon Motor 409510, which can provide of 5 A continuous current and 15 A peak current and be responsible for one electromagnetic coil so that the current in each coil can be controlled independently. The DAC is used as a gateway to convert digital signals from the sensor card to analog signals and delivery them to the amplifiers. The sensor card is generally equipped in the computer with the installation of magnetic field controlling program. For example, a Sensoray card 826 is used in the hardware of Magdisk to generate voltage signals according to the instructions from a self-developed Lab View-based magnetic field controlling program.

Figure 15:
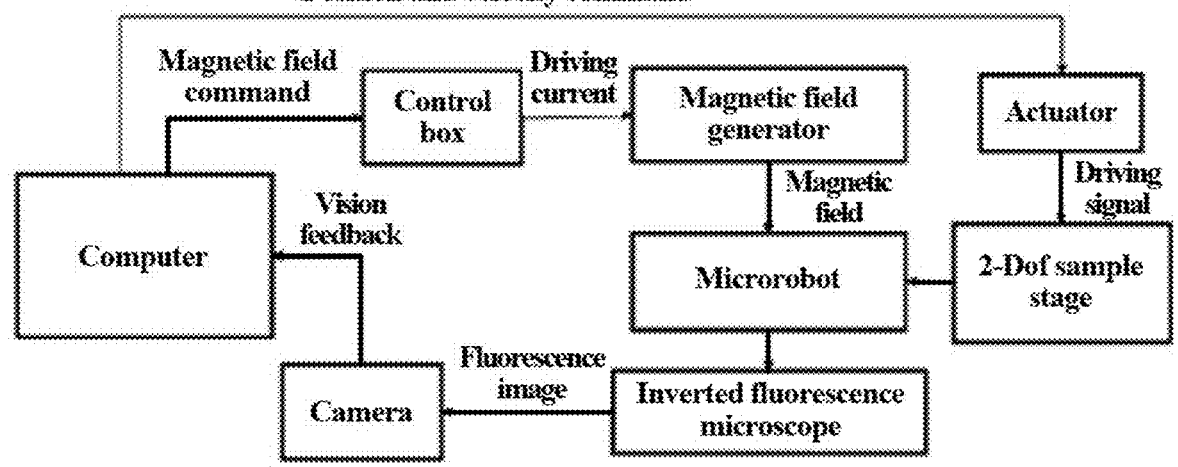
FIG. 15 is a control scheme, which is based on a core computer and a series of equipment.

The software system includes a control scheme and a related executing program. FIG. 15 give a control scheme, which is based on a core computer and a series of hardware. The computer sends a magnetic field command to a controller box, which delivers a driving current to the magnetic field generator, e.g., Magdisk. Meanwhile, the computer also sends position and velocity command to the actuators of a two degree-of-freedom sample stage, which will execute driving signal to move the microrobots with the optimal performance to the region of magnetic field generator with the maximum strength. Magnetic field generator would exert an expected magnetic field to propel the microrobots according to the program. The motion status of the microrobot can be observed by an inverted fluorescent microscope equipped with a fluorescent camera, which will be feedbacked to the computer through a series of fluorescent images, finally determining the executed results of the delivered commands. In embodiments, the imaging sensor, e.g. camera, mounted on the microscope captures the current image of the microscope, which is then transmitted to the computer. This process feeds back the microrobot motion status to the computer by images. Then image processing may be used to extract the current position of the microrobots which are used in the motion controller. The imaging feedback is used for two aspects. Firstly, the imaging feedback is used to evaluate the optimal microrobots for fluorescence observation and initial optimized recognition. Secondly, the imaging feedback is employed to control the magnetic field generator for tracking trajectory.

Figure 16:
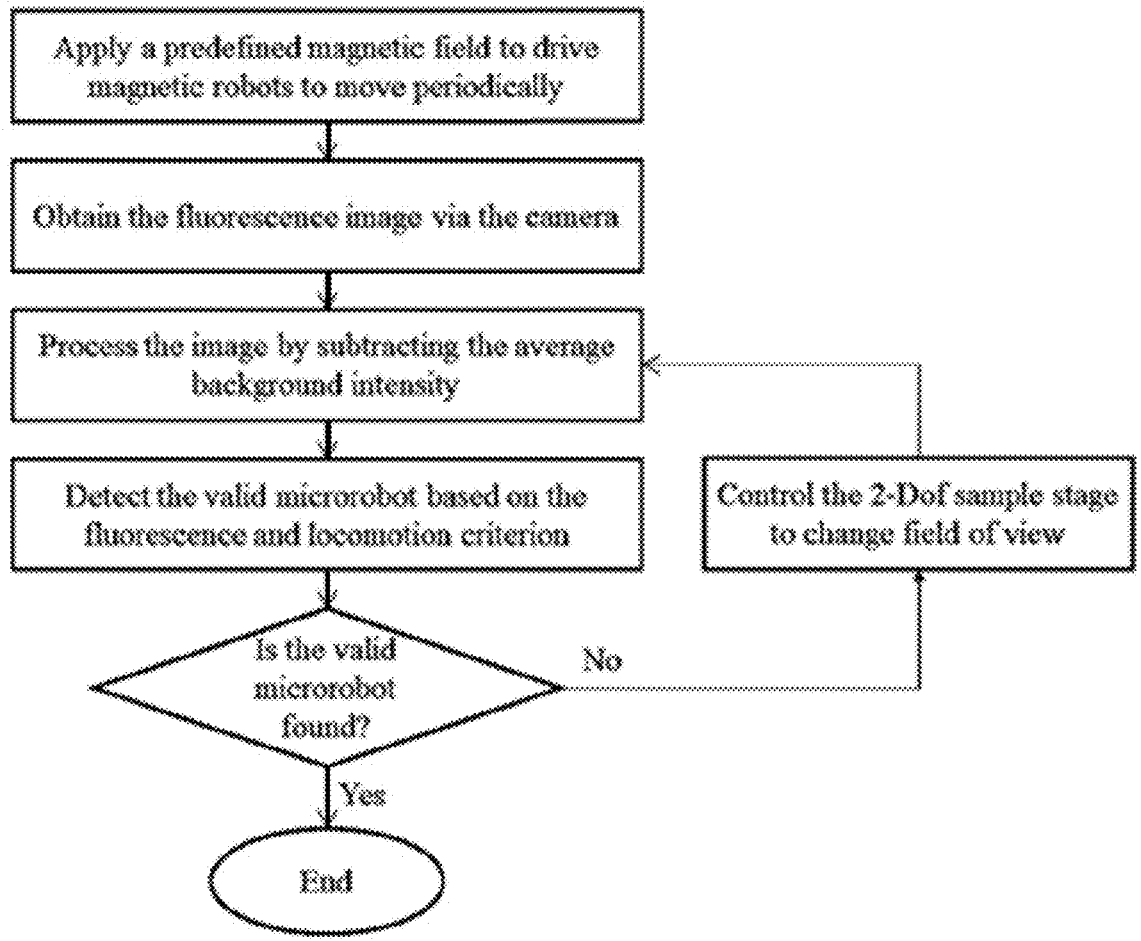
FIG. 16 is a schematic illustration of the algorithm of automated recognition.

The related executing program includes two aspects. One is the auto-recognition program-based algorithm as shown in FIG. 16. The fluorescent intensity of the functionalized microrobots is obtained and evaluated by subtracting the average background. A subset of the microrobots in a test sample are determined to be valid microrobots. Valid microrobots are the ones with an initial fluorescence intensity that is above a predetermined threshold. The initial fluorescence of the microrobots in a test sample may be measured prior to propelling the microrobots with the magnetic field.

Figure 17:
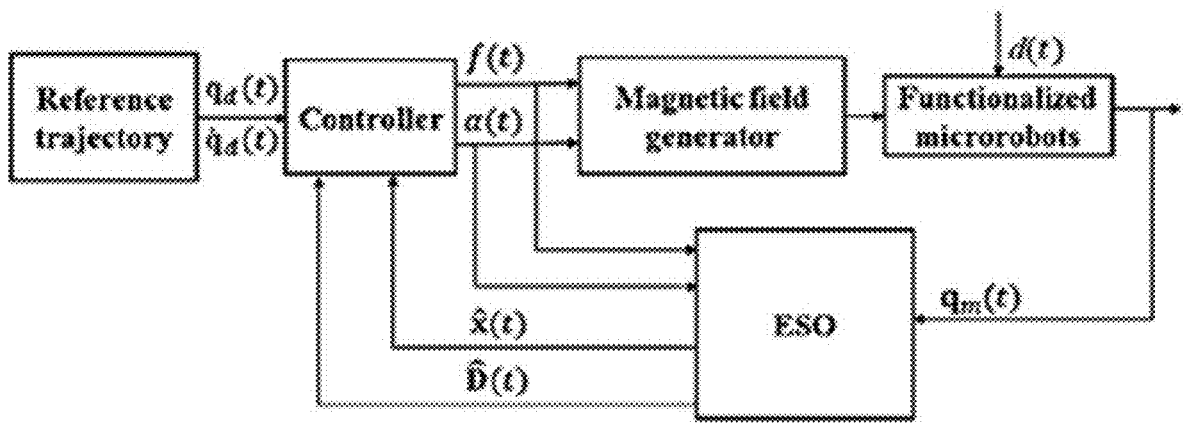
FIG. 17 is a schematic illustration of the algorithm of automated control.

A second aspect is an auto-tracking program for automation based on an algorithm as shown in FIG. 17. The desired trajectory of the microrobot, also called reference trajectory, can be dependent on $q_d(t)$ and $dot(q_d(t))$ functions, which represent the desired position and velocity. These functions can be sent by the controller and executed in the following form.

$$\begin{cases} f_x(t) = K_1(q_{d_x}(t) - \hat{q}_x(t)) + \frac{1}{a_0}\dot{q}_{d_x}(t) - \frac{1}{a_0}\hat{D}_x(t) \\ f_y(t) = K_2(q_{d_y}(t) - \hat{q}_y(t)) + \frac{1}{a_0}\dot{q}_{d_y}(t) - \frac{1}{a_0}\hat{D}_y(t) \\ f(t) = sat\left(\sqrt{f_x^2(t) + f_y^2(t)}, f_{max}\right) \\ \alpha(t) = \arctan2(f_y(t)/f_x(t)) \end{cases}$$

where $K_i$ (i=1, 2) are positive control gains tuned by discrete-time simulations with the real control frequency, and sat(a, b) is a saturation function defined as:

$$sat(\sigma, b) = \begin{cases} \sigma, & \sigma \leq b \\ b, & \sigma > b \end{cases}$$

At the same time, an extended state observer (ESO) provides feedback to the real motion state for calibrating the control motion, which conforms to the following equation. ESO not only estimates the motion states of the microrobots, but also to evaluate the generalized disturbances for compensation. The precision of final trajectory tracking is around 3 micrometers.

$$\begin{cases} \dot{\hat{x}}_1(t) = \hat{x}_2(t) + a_0 f(t)\cos(\alpha(t)) + \frac{\beta_1}{\epsilon}(q_{xm}(t) - \hat{x}_1(t)) \\ \dot{\hat{x}}_2(t) = \frac{\beta_2}{\epsilon^2}(q_{xm}(t) - \hat{x}_1(t)) \\ \dot{\hat{x}}_3(t) = \hat{x}_4(t) + a_0 f(t)\sin(\alpha(t)) + \frac{\beta_3}{\epsilon}(q_{ym}(t) - \hat{x}_3(t)) \\ \dot{\hat{x}}_4(t) = \frac{\beta_4}{\epsilon^2}(q_{ym}(t) - \hat{x}_3(t)) \end{cases}$$

Figure 18:
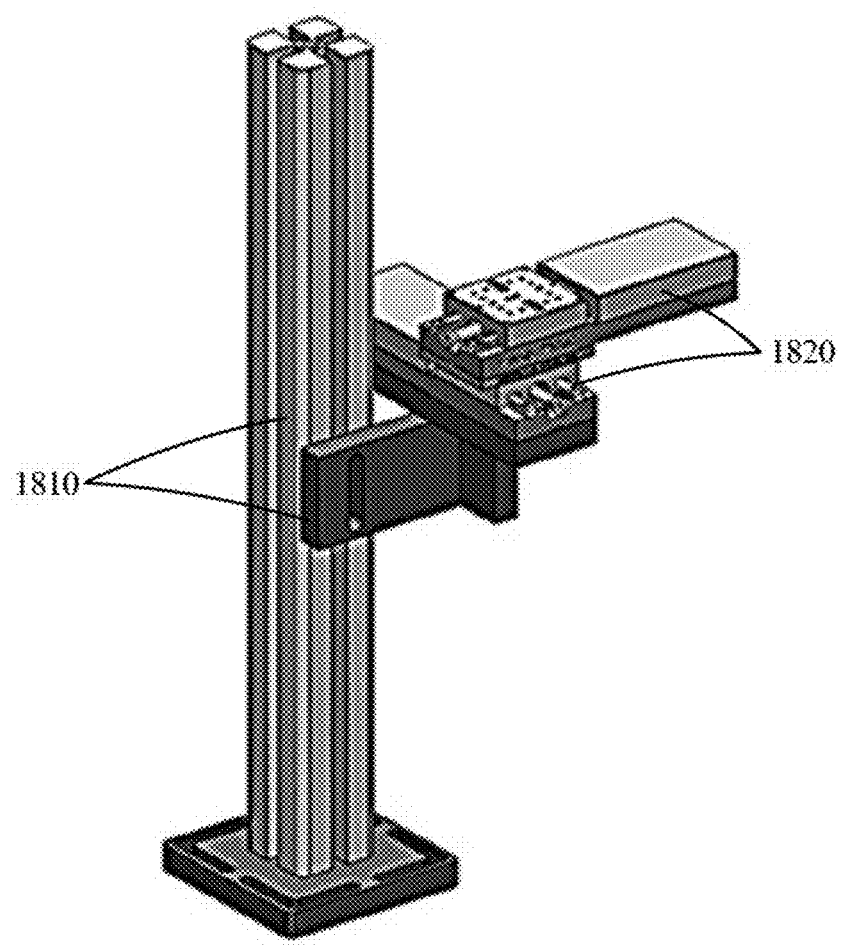
FIG. 18 is a motorized sample platform for automated control of the disclosed microrobots for detection.
Figure 19:
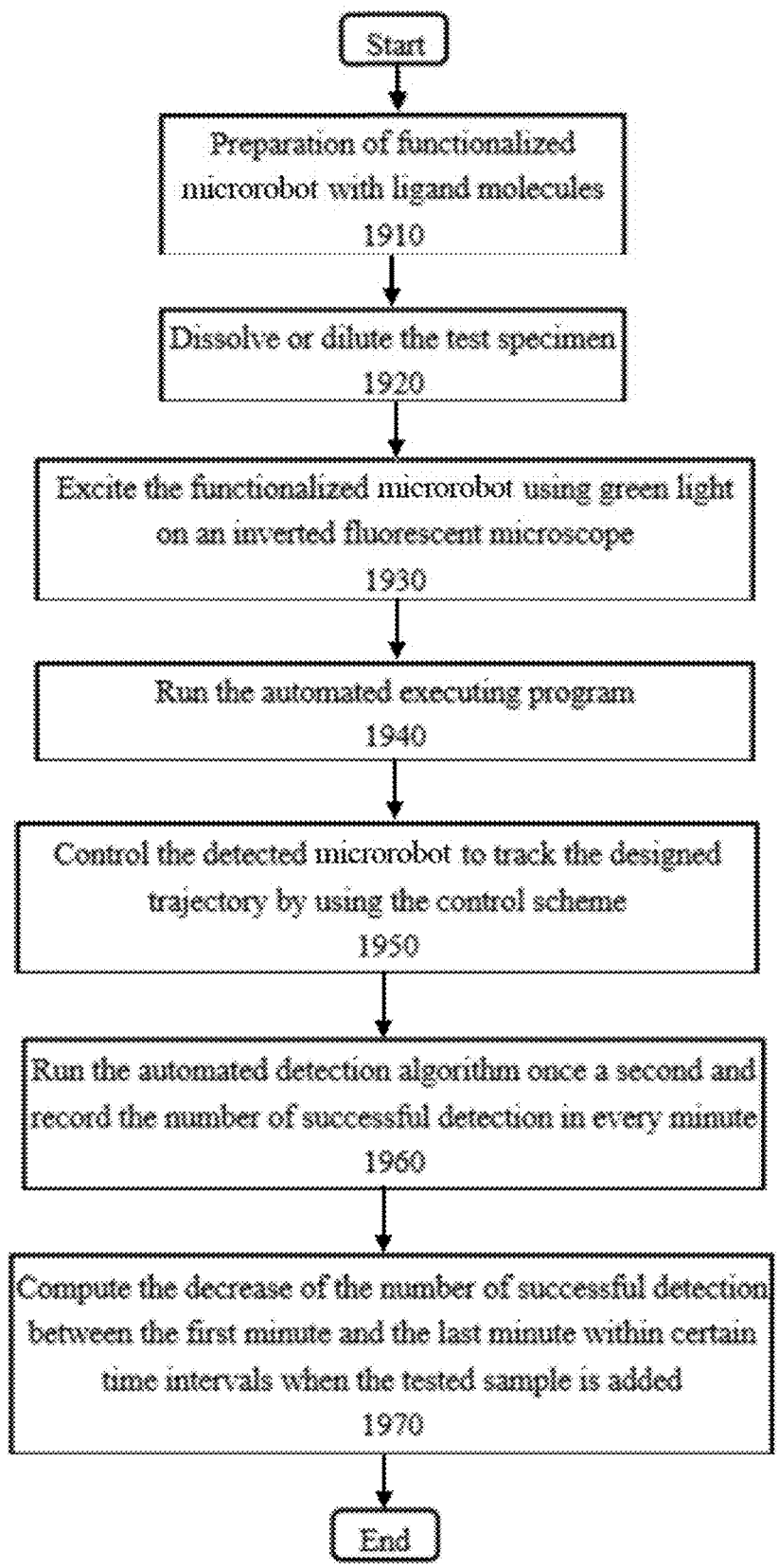
FIG. 19 is a process flow diagram of an exemplary process for automated detecting toxin targets using the disclosed functionalized microrobot in a motion control system equipped with an inverted fluorescent microscope.

A motorized sample platform 1323 is connected to the motion control system for initial optimal recognition and the following automated detection. As shown in FIG. 18, the motorized sample platform includes a supporter (1810) and two motorized translation stages bundled with controller and power supply (1820). Two translation stages are placed orthogonally and overlappingly, which can separately provide a X axial and Y axial motion which can be achieved through manual or automated operation. Such an arrangement will achieve the XY-plane movement of the functionalized microrobots in manual or automated mode via controller system.

Figure 20:
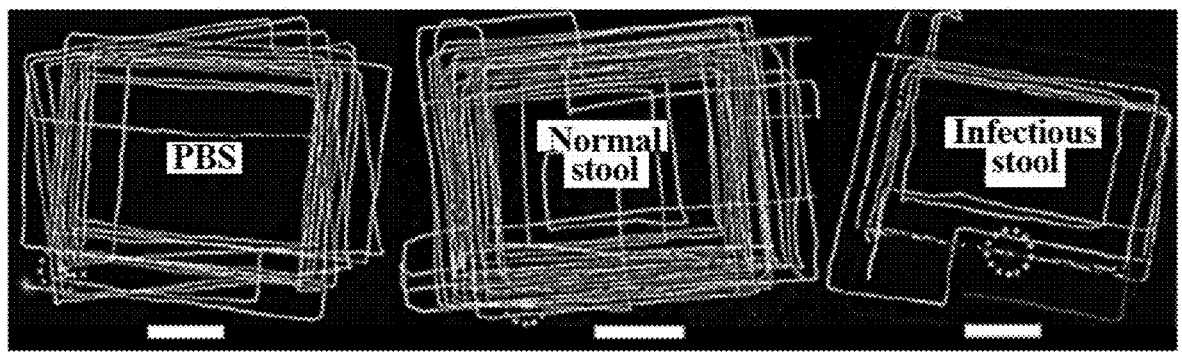
FIG. 20 shows the tracking fluorescence trajectory in PBS, normal stool supernatant, C. diff-infected patient's stool supernatant using the disclosed detection system combined with an inverted fluorescent microscope in manual operation mode.
Figure 21:
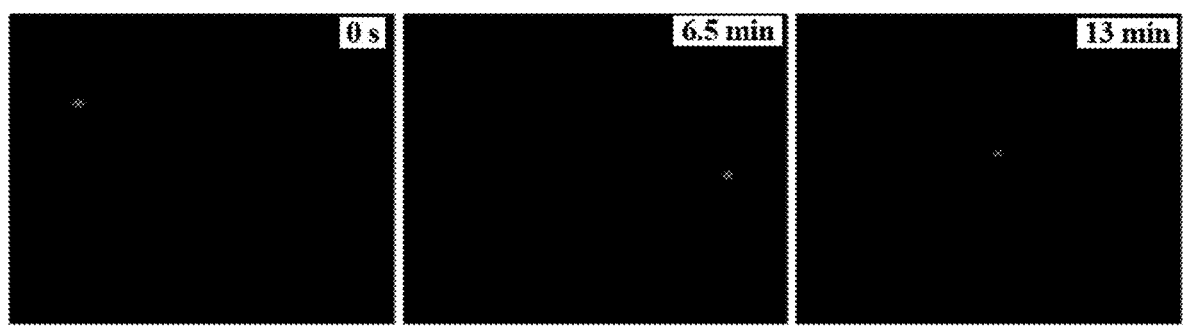
FIG. 21 shows the time-lapse images of the disclosed functionalized microrobot in C. diff-infected patient's stool supernatant in automated operation mode using the disclosed detection system combined with an inverted fluorescent microscope in automated operation mode.

When the above disclosed parts are integrated, the formed whole system can detect the presence of bacteria toxin in a practical specimen with the inverted fluorescent microscope or a fluorescent multi-reader. For example, FIG. 18 gives a process flow diagram of an exemplary process for detecting C. diff toxin targets in a clinical stool samples using the detection system equipped with an inverted fluorescent microscope. Initially, the preparation of the oligosaccharide-functionalized microrobot is performed (1910). The pre-treatment of the stool samples includes the dissolution or/and dilution of them (1920). Next, the functionalized microrobots is excited under green light excitation on an inverted fluorescent microscope (1930). The automated recognition program is firstly used to search the test sample for optimal fluorescent microrobots (1940) with a fluorescence above a predetermined threshold. Afterward, the automated control scheme is used to control the detected microrobots to track the designed trajectory (1950). The automated recognition algorithm is re-run once a second and record the number of successful detection in every minute (1960). Finally, the presence of a target molecule, for example C. diff toxins, in the test sample, for example pre-treated stool supernatant, can be detected by observing the fluorescent quenching of the microrobots within certain time intervals and computing the decrease of the number of successful detection between the first minute and the last minute within certain time intervals when the tested sample is added (1970). Detecting a presence of the target toxins in a tested specimen can include detecting a concentration of the target toxin based on fluorescent quenching induced by a motion of the microrobot. Detecting a presence of the target toxins in a tested fluid based on fluorescent quenching can include providing the functionalized microrobot with fluorescent sensing probe to allow the microrobot to form a complex between the sensing probe and the target toxins. According to the disclosed detection process, the detecting system and the related recognition and detection methods can be employed to sense the bacteria toxins in various fluid, even clinical samples. For example, the tracking fluorescence trajectories in PBS and normal stool supernatant are exemplarily illustrated in FIG. 20 using the disclosed detecting system combined with an inverted fluorescent microscope in manual operation mode. For example, the motion trajectories of oligosaccharide-functionalized microrobots can be tracked clearly with continuous motion for about 20 mins. There is no fluorescent quenching to be observed on oligosaccharide-functionalized microrobot, suggesting the absence of C. diff toxins in PBS and normal stool supernatant. When the C. diff-infected patient's stool supernatant is tested, the tracking fluorescence trajectory using the same mode is shown in FIG. 20. The motion trajectories of oligosaccharide-functionalized microrobots decreases dramatically, which can be tracked hardly with continuous motion for about 20 mins. Moreover, the obvious fluorescent quenching is observed with long-time motion, indicating the presence of C. diff toxins in C. diff-infected patient's stool supernatant. Thus, the detecting system can rapidly and selectively detect the toxins from complex samples in manual mode. Such a detection ability can be completed by automated motion according to pre-designed path and real-time recording with observing camera, greatly reducing the manpower. For example, FIG. 21 gives the automated tracking fluorescence trajectory in C. diff-infected patient's stool supernatant using the disclosed detecting system combined with an inverted fluorescent microscope and camera. The obvious fluorescent quenching of oligosaccharide-functionalized microrobot can be observed in C. diff-infected patient's stool supernatant with the time going, exhibiting a good and rapid sensing ability of detecting system.

The invention claimed is:
1. A steerable micro-robot comprising:
 a core with a widest dimension less than 20 microns, wherein the core is a naturally occurring biological material;
 a magnetic coating on a surface of the core; and a detection probe coating on the surface of the magnetic coating, wherein the detection probe coating comprises carbon dots functionalized with targeting ligands configured to specifically bind to target molecules.

2. The steerable micro-robot of claim 1, wherein the naturally occurring biological material comprises an inactivated bacterial spore, an inactivated fungal spore, or an inactivated plant spore.

3. The steerable micro-robot of claim 1, wherein the magnetic coating comprises magnetic nanoparticles.

4. The steerable micro-robot of claim 1, wherein the magnetic coating defines a thickness of about 50 nm to 200 nm.

5. The steerable micro-robot of claim 1, further comprising a self-assembled monolayer, wherein the self-assembled monolayer functionalizes the magnetic coating.

6. The steerable micro-robot of claim 1, wherein the targeting ligands comprise oligosaccharides, aptamers, or phenylboronic acid.

7. The steerable micro-robot of claim 1, wherein the targeting ligands are configured to bind to the target molecules, wherein the target molecules comprise at least one of:

toxins associated with at least one of toxin A or toxin B of *Clostridium difficile* bacteria;

endotoxins of Gram-negative bacteria;

mycotonxin;

ochratoxin A;

fumonisine B1; and plant ricin B toxin.

8. The steerable micro-robot of claim 7, wherein the detection probe coating is configured to emit or quench florescence upon binding with the target molecules.

9. A system for detecting bacteria in a test sample with a plurality of steerable micro-robots according to claim 1, the system comprising:

the plurality of steerable micro-robots;

a sample holder configured to receive the test sample and the plurality of steerable micro-robots;

a magnetic field generator configured to steer the plurality of steerable micro-robots in the test sample with a magnetic field; and an imaging device configured to sense fluorescence of the plurality of steerable micro-robots while being steered in the test sample.

10. The system of claim 9, further comprising a a controller, wherein the controller is configured to provide dynamic currents to the magnetic field generator in order to steer the plurality of steerable micro-robots in the test sample.

11. The system of claim 10, further comprising:

a sample stage with at least two degrees of freedom, wherein the sample stage is coupled to the sample holder;

wherein the controller is configured to simultaneously cause the sample stage to move relative to the imaging device and cause the plurality of steerable micro-robots to be steered in the test sample in order to determine with the imaging device a subset of the plurality of steerable micro-robots having a brightest fluorescence.

12. A method of producing a steerable micro-robot of claim 1, comprising:

coating the biological material core with a magnetic coating on a surface of the core; and coating the magnetic coating coated the core with the detection probe coating comprises carbon dots functionalized with targeting ligands.

13. The method of claim 12, further comprising removing impurities on an exine and internal core substances of the core prior to coating the core with the magnetic coating, wherein the core is a bacterial, fungal or plant spore that has been inactivated.

14. A method of detecting bacteria in a test sample with the steerable micro-robot of claim 1, comprising:

sensing the fluorescence emitted by the carbon dots of the steerable micro-robot in a test sample with an image sensor.

15. The method of claim 14, further comprising continuously moving the steerable micro-robot with a rotating magnetic field generating by a magnetic field generator.

16. The method of claim 15, wherein continuously moving the steerable micro-robot comprises controlling spin, rotation-translate, and/or tumble.

17. The method of claim 15, wherein continuously moving the steerable micro-robot comprises moving the magnetically steerable micro-robot around a pre-determined path.

18. The method of claim 14, wherein sensing the fluorescence comprises detecting, with the image sensor, fluorescent quenching caused by the detection probe coating binding to a toxin indicating the presence of a bacteria associated with the toxin.

19. A method of detecting bacteria in a test sample with a plurality of steerable micro-robots according to claim 1, the method comprising:

determining a subset of the plurality of steerable micro-robots by sensing which of the plurality of steerable micro-robots in the test sample has a brightest fluorescence with an image sensor;

continuously moving the subset of the plurality of steerable micro-robots in the test sample with a rotating magnetic field generated by a magnetic field generator; and sensing fluorescence of the continuously moving subset of steerable micro-robots in the test sample with the image sensor.

20. The method of claim 19, wherein determining the subset of the plurality of steerable micro-robots comprises moving the test sample relative to the image sensor with a sample stage with at least two degrees of freedom while the image sensor senses fluorescence of the plurality of steerable micro-robots.

* * * * *